United States Patent
Mueller et al.

(10) Patent No.: US 7,449,560 B2
(45) Date of Patent: Nov. 11, 2008

(54) PHOSOPHOINOSITOGLYCAN BINDING PROTEINS

(75) Inventors: Guenter Mueller, Sulzbach (DE); Wendelin Frick, Huenstetten-Beuerbach (DE); Stefan Petry, Frankfurt (DE); Rudolf Schneider, Niedernhausen (DE); Matthias Urmann, Eschborn (DE)

(73) Assignee: Sanofi-Aventis Deutschland GmbH, Frankfurt Am Main (DE)

( * ) Notice: Subject to any disclaimer, the term of this patent is extended or adjusted under 35 U.S.C. 154(b) by 202 days.

(21) Appl. No.: 11/377,531

(22) Filed: Mar. 16, 2006

(65) Prior Publication Data

US 2006/0160142 A1  Jul. 20, 2006

Related U.S. Application Data

(62) Division of application No. 10/470,606, filed on Jul. 3, 2003, now Pat. No. 7,049,416.

(30) Foreign Application Priority Data

Jul. 5, 2002 (EP) .................................. 02015047

(51) Int. Cl.
*C07K 1/00* (2006.01)
*C07K 14/00* (2006.01)
*C07K 16/00* (2006.01)
*C07K 17/00* (2006.01)

(52) U.S. Cl. .......................... 530/413; 530/412; 435/7.1

(58) Field of Classification Search ................. 530/413, 530/412; 435/7.1
See application file for complete search history.

(56) References Cited

FOREIGN PATENT DOCUMENTS

EP          0532915        1/1997

OTHER PUBLICATIONS

Weid et al., Convergence and divergence of the signaling pathways for insulin and phosphoinositolglycans.Mol Med. May 1998;4(5):299-323.*
Frick et al., Insulin-mimetic signalling of synthetic phosphoinositolglycans in isolated rat adipocytes.Biochem J. Nov. 15, 1998;336 ( Pt 1):163-181.*
Muller et al., Phosphoinositolglycan-peptides from yeast potently induce metabolic insulin actions in isolated rat adipocytes, cardiomyocytes, and diaphragms. Endocrinology. Aug. 1997;138(8):3459-3475.*
Kessler et al., Signalling pathways of an insulin-mimetic phosphoinositolglycan-peptide in muscle and adipose tissue. Biochem J. Feb. 15, 1998;330 (Pt 1):277-286.*
Alexandra Kessler et al., Signaling pathways of an insulin-mimetic phosphoinositolglycan-peptide in muscle and adipose tissue, Biochem J. 1998, pp. 277-286, vol. 330.
Gunter Muller et al., Convergence and Divergence of the Signaling Pathways for Insulin and Phophoinositolglycans, Molecular Medicine, 1998, pp. 299-323, vol. 4.
Gunter Muller et al., Insulin-Mimetic Signaling by the Sulfonylurea Glimepiride and Phosphoinositolglycans Involves Distinct Mechanisms for Redistribution of Lipid Raft Components, Biochemistry, 2001, pp. 14603-14620, vol. 40.
Gunter Muller et al., Interaction of phosphoinositolglycan (-peptides) with plasma membrane lipid rafts of rat adipocytes, Archives of Biochemistry and Biophysics, 2002, pp. 17-32, vol. 408.
Gunter Muller et al., Phosphoinositolglycan-Peptides from Yeast Induce Metabolic Insulin Actions in Isolated Rat Adipocytes, Cardiomyocytes and Diaphragms, Endocrinology, 1997, pp. 3459-3475, vol. 138, No. 8.
Gunter Muller et al., Redistribution of Glycosyl-Phosphatidylinositol-anchored Proteins from Caveolae as Potential Target for Signal Transduction Therapy, European Journal of Cell Biology, 1999, p. 73, vol. 78, No. 49.
Gunter Muller et al., Redistribution of Signaling Proteins from Caveolae as Potential Target for Insulin-Mimetic Compounds, Diabetics Research and Clinical Practice, 2000, p. S157, vol. 50, No. 1.
Gunter Muller et al., Signaling via caveolin: involvement in the cross-talk betweeen phosphoinositolglycans and insulin, CMLS, Cell. Mol. Life Sci., 1999, p. 945-970, vol. 56.
Gunter Muller et al., Cross Talk of pp125 FAK and P59Lyn Non-Receptor Tyrosine Kinase to Insulin-Mimetic Signaling in Adipocytes, Molecular and Cellular Biology, 2000, pp. 4708-4723, vol. 20, No. 13.
Gunter Muller et al, Cholesterol Depletion Blocks Redistribution of Lipid Raft Components and Insulin-Mimetic Signaling by Glimepiride and Phosphoinositolglycans in Rat Adipocytes, Molecular Medicine, vol. 8, No. 3, Mar. 2002, pp. 120-136.
Morris et al., Sortilin Is the Major 110-kDa Protein in GLUT4 Vesicles from Adipocytes, Journ of Biological Chemistry, vol. 273, No. 6, Feb. 6, 1998, pp. 3582-3587.
Wendelin Frick et al., Insulin-mimetic signaling of synthetic phosphoinositolyglycans in isolated rat adipocytes, Biochem J. 1998, pp. 163-181, vol. 336.
Wendelin Frick et al., Structure-Activity Relationship of Synthetic Phosphoinositolglycans Mimicking Metabolic Insulin Action, Biochemistry, 1998, pp. 13421-13436, vol. 37.

* cited by examiner

*Primary Examiner*—Tekchand Saidha

(57) ABSTRACT

The invention refers to a protein from plasma membrane of adipocytes. The protein has specific binding affinity to phosphoinositoylglycans. It regulates glucose uptake by circumventing the insulin signaling cascade.

5 Claims, 20 Drawing Sheets

7 xii

YCN

PHOSOPHOINOSITOGLYCAN BINDING PROTEINS

CROSS REFERENCE TO RELATED APPLICATIONS

This application is a divisional of U.S. patent application Ser. No. 10/470,606 filed on Jul. 3, 2003, now U.S. Pat. No. 7,049,416, issued May 23, 2006; this application claims priority under 35 U.S.C. § 119 to EP 02015047.0 filed Jul. 5, 2002, the disclosure of which is incorporated herein by reference in its entirety.

BACKGROUND OF THE INVENTION

1. Field of the Invention

The invention relates to a protein from plasma membranes of adipocytes which has specific binding affinity to phosphoinositolglycans.

2. Description of the Background

The role of phospholipids and phospholipases in transmembrane signaling is firmly established. Equally well-established is the concept of anchoring proteins into cell membranes through a covalently linked glycosylphosphatidylinositol (GPI), and the precise chemical structure of the GPI anchor has been worked out for several GPI-anchored proteins, such as acetylcholinesterase (AchE) from human erythrocytes, rat Thy-1, and several coat proteins of parasites like the variant surface glycoprotein (VSG) from Trypanosoma brucei. Lipid anchoring occurs through phosphatidylinositol (PI), which consists of a diacyl- or an alkylacyl glycerol type phospholipid. Since the latter occurs, among others, in mammalian anchors, and differs from the bulk PI present in membranes, it could provide a novel molecular species involved in the generation of second messengers derived from GPIs. Signaling by GPIs is of special interest as these lipid-anchored molecules do not span the membrane, but in most cases are embedded in the outer half of the lipid bilayer. The signal-mediated release from the cell membrane of GPIs has been demonstrated for a variety of endocrine and paracrine molecules, ranging from hormones to growth factors. The involvement of GPIs in transmembrane signaling and their intracellular effects seems by now established, but little is known about the signaling pathway leading to the observed metabolic effects.

The notion that GPI-anchored molecules possess signaling properties results from early experiments in which it was shown that the binding of insulin to its receptor activates the hydrolysis of GPIs. A low-molecular-weight substance was identified that mimics certain actions of insulin on metabolic enzymes. This substance has an inositol glycan structure and is produced by the insulin-sensitive hydrolysis of a GPI in the plasma membrane. Although the GPI precursor for the inositol glycan enzyme modulator was originally thought to be structurally analogous to the GPI membrane protein anchor, there are distinct differences in the carbohydrate moiety between the signal transducing GPI and the GPI anchor of membrane proteins. The GPI-membrane protein anchor invariably consists of the trimannose core followed by an ethanolamine phosphate, which provides the link to the C-terminal amino acid of the attached protein.

Regulated GPI hydrolysis is not only restricted to insulin but has been observed with a number of other hormones.

In practically all cases, the stimulation of cells by hormones or growth factors leads to a transient release of GPI-anchored proteins from the cell surface. Most of the receptors for these agonists are either tyrosine kinase receptors or receptors coupled to tyrosine kinases.

Many of the proteins involved in insulin action have been identified at the molecular level. The insulin receptor is a transmembrane tyrosine kinase, which when activated by insulin binding, undergoes rapid autophosphorylation and phosphorylates a number of intracellular substrates, among them one or more 50-60 kDa proteins, including the Shc, a 15 kDa fatty acid binding protein and several so-called insulin receptor substrate proteins, IRS-1/2/3/4. After tyrosine phosphorylation, the IRS polypeptides act as docking proteins for several Src homology 2 domain-containing adaptor molecules and enzymes, including phosphatidylinositol 3-kinase (PI 3-K), Grb2, SHP2, Nck, and Fyn. The interaction between the IRS proteins and PI 3-K occurs through the p85 regulatory subunit of the enzyme and results in an increase in catalytic activity of the p110 subunit. PI 3-K is essential for many insulin-sensitive metabolic processes, including stimulation of glucose transport and glycogen synthesis. In all cases in which there is stimulation of tyrosine phosphorylation of IRS proteins, there is concomitant docking of these proteins to the p85 subunit of PI 3-K and, with the exception of the cross-talk between the insulin and angiotensin signaling systems, this docking was associated with stimulation of PI 3-K activity.

In addition to the identification of the signal-transduction pathways leading directly from the insulin receptor to downstream targets, several cross-talks have been delineated between signaling transmission by insulin and other hormones/growth factors or diverse exogenous stimuli, which either mimic (to a certain degree) or modulate in a positive or negative fashion metabolic and/or mitogenic insulin action in various cellular systems. Since none of these ligands activates the insulin receptor kinase directly, their signaling pathways may converge with that of insulin at a more distal signaling step. This property is shared by phosphoinositolglycan-peptide (PIG-P) molecules of different type as for example for PIG-P prepared from the glycosylphosphatidylinositol anchor of yeast Gce1p which mimic metabolic insulin action to a significant degree without concomitant induction of insulin receptor kinase activity.

Positive cross-talk of phosphoinositolglycans (PIG) and PIG-peptides (PIG-P) to the insulin signal transduction cascade in insulin-responsive target cells involves redistribution of glycosylphosphatidylinositol (GPI)-anchored plasma membrane proteins (GPI protein) and dually acylated non-receptor tyrosine kinases from detergent-resistant glycolipid-enriched plasma membrane raft domains of high cholesterol content (hcDIGs) to rafts of lower cholesterol content (lcDIGs).

In isolated rat adipocytes the primary target of PIG-P is localized in hcDIGs. Radiolabeled PIG-P, Tyr-Cys-Asn-NH—$(CH_2)_2$—O—PO(OH)O-6Man$\alpha$1-2)2Man$\alpha$1-6Man$\alpha$1-4GluN1-6Ino-1,2-(cyclic)-phosphate (YCN-PIG) as well as radiolabeled and lipolytically cleaved GPI protein (lcGce1p) from *Saccharomyces cerevisiae*, from which YCN-PIG has been derived, bind to hcDIGs in saturable fashion but not to lcDIGs, microsomes or total plasma membranes. Binding of both YCN-PIG and lcGce1 is specific, as it is completely abolished either by excess of chemically synthesized unlabeled YCN-PIG or by pretreatment of the adipocytes with trypsin and subsequent NaCl or N-ethylmaleimide (NEM) indicating that YCN-PIG is recognized by a cell surface receptor. Binding of PIG-P is considerably increased in hcDIGs from adipocytes pretreated with GPI-specific phospholipases C compatible with lipolytic removal of endogenous ligands, such as GPI proteins/lipids. Binding affinity is highest for YCN-PIG, followed by the combination of the separate constituents, Tyr-Cys-Asn-NH—(CH$_2$)$_2$—OH(YCN) plus HO—PO(H)O-6Man$\alpha$1 (Man$\alpha$1-2)-2-Man$\alpha$1-6Man$\alpha$1-4GluN1-6Ino-1,2-(cyclic)-phosphate (PIG37), and the peptide variant, YMN-PIG. PIG37 and YCN alone exhibit intermediate and low affinity. Incubation of adipocytes with YCN-PIG diminishes subsequent labeling by [$^{14}$C]NEM of the 115 kDa polypeptide released from the cell surface by sequential trypsin/NaCl-treatment. These data show that in rat adipocytes insulin-mimetic PIG(-P) are recognized by a trypsin/NaCl/NEM-sensitive 115 kDa protein of hcDIGs which acts as receptor for GPI proteins.

Several types of DIGs seem to exist in the same cell. Caveolae represent special DIGs in terminally differentiated cells which form flask-shaped invaginations driven by the abundant expression of the marker and structural protein, caveolin 1-3.

Caveolae which account for 20% of the plasma membrane surface area in adipocytes participate in receptor-mediated potocytosis, endocytosis, transcytosis and signal transduction. In isolated rat adipocytes IcDIGs of low cholesterol/caveolin content exhibiting high buoyant density (according to sucrose density gradient centrifugation) can be discriminated from typical hcDIGs with high cholesterol/caveolin content characterized by low buoyant density. The major fraction of GPI proteins, such as Gce1 and Nuc, as well as of dually acylated proteins, such as the NRTK Non Receptor Tyrosine Kinase, pp59$^{Lyn}$, are located at hcDIGs. In response to insulin-mimetic stimuli such as synthetic PIG or the sulfonylurea, glimepiride, both GPI proteins and NRTKs are translocated from hcDIGs to IcDIGs. This redistribution is not caused by loss of their lipid modification.

The polar core glycan head group without (PIG) or with (PIG-P) adjacent amino acids from the carboxyl-terminus of the GPI protein polypeptide moiety provides the molecular basis of the distribution of GPI proteins between hcDIGs and IcDIGs in the basal state and their redistribution in response to insulin-mimetic stimuli.

GPI proteins are cell surface antigens, ectoenzymes, receptors or cell adhesion molecules expressed in eucaryotes from yeast to man and anchored to the outer leaflet of the plasma membrane by a covalently attached glycosylphosphatidylinositol (GPI) lipid moiety. Despite the lack of a transmembrane domain, they have been implicated in signal transduction across the plasma membrane.

The finding that GPI proteins associate with specialized lipid raft domains, so-called detergent-insoluble glycolipid-enriched rafts, DIGs, rather than with distinct transmembrane binding/linker proteins demonstrates the possibility of lipid-lipid interactions as the major coupling mechanism for signal transduction mediated by GPI proteins.

The basic structural element of DIGs is a lateral assembly of (glyco)sphingolipids and cholesterol which adopts a liquid-ordered (I$_o$) organization distinct from that of adjacent liquid-disordered (I$_d$) regions in the membrane lipid bilayer. The plasma membranes of mammalian cells contain cholesterol (30-50 mol %) and a mixture of lipids with preference for the I$_d$ domains (e.g. phosphatidylcholines with unsaturated tails) and lipids bearing saturated acyl chains with preference for I$_o$ domains (e.g. [glyco]sphingolipids and GPI lipids). Cholesterol is thought to contribute to the tight packing of lipids in I$_o$ domains by filling interstitial spaces between lipid molecules, and the formation of I$_o$ domains is seen only within certain ranges of cholesterol concentration.

Insulin is a very important hormone, which exerts a significant effect on the metabolism of the body. In the general terms it promotes anabolic processes and inhibits catabolic processes. Specifically it increases the rate of synthesis of glycogen, fatty acids and protein, and inhibits the breakdown of protein and glycogen. A vital action of the hormone is to stimulate cells from a liver, muscle and fat to remove glucose, some other sugars and amino acids from the blood.

Bovine insulin consists of two polypeptide chains, polypeptide A containing 21 AA and polypeptide B containing 30 AA, which are joined by two —S—S— (disulfide bridges). This same structural pattern occurs in insulin of many mammals including humans.

The structure is compact cylinder-like with only the carboxyl end of the B chain sticking out from the rest of the protein. There are many hydrophobic residues, which interact to form a central hydrophobic core, and interdispersed are some polar residues on either side that further stabilize the protein. Three disulfide bridges clamp the structure together, two inter-chain and one intra-chain.

A common feature in the biosynthesis of many proteins, but in particular for proteins exported from cells, is that the protein is produced in a precursor form then modified to produce the final form during storage and before release. Insulin is synthesized by a group of cells in the pancreas called Islets of Langerhans, stored in granules then released into the blood when required.

When insulin is first synthesized it consists of a 100 AA single polypeptide chain consisting of a signal sequence of 16 AA, a B chain, a C chain called connecting chain of 33 AA, and a A chain. This structure is called pre-proinsulin (PPI). It is thought that the signal region is responsible for directing the PPI from the site of synthesis to the ER (endoplasmic reticulum) in the cell, which collect and package the insulin to form storage granules. When located in the ER, the signal peptide is removed by a protease enzyme.

Diabetes mellitus is a chronic disease that requires long-term medical attention both to limit the development of its devastating complications and to manage them when they do occur. Diabetes is associated with acute and chronic complications as hypoglycemia, diabetic ketoacidosis and hyperosmolar non-ketotic syndrome.

Type 1 diabetes generally occurs in young, lean patients and is characterized by the marked inability of the pancreas to secrete insulin because of autoimmune destruction of the beta cells. The distinguishing characteristics of a patient with type 1 diabetes is that if insulin is withdrawn, ketosis and eventually ketoacidosis develop. These patients are, therefore, dependent on exogenous insulin to sustain their lives.

Type 2 diabetes typically occurs in individuals older than 40 years who have a family history of diabetes. Type 2 diabetes is characterized by peripheral insulin resistance with an insulin-secretory defect that varies in severity. These defects lead to increased hepatic gluconeogenesis, which produces fasting hyperglycemia. Most patients (90%) who develop type 2 diabetes are obese, and obesity itself is associated with insulin resistance, which worsens the diabetic state.

A variety of other types of diabetes, previously called "secondary diabetes", are caused by other illnesses or medications. Depending on the primary process involved (i.e., destruction of pancreatic beta cells or development of peripheral insulin resistance), these types of diabetes behave similarly to type 1 or type 2 diabetes. The most common are diseases of the pancreas that destroy the pancreatic beta cells (e.g., hemochromatosis, pancreatitis, cystic fibrosis, pancreatic cancer), hormonal syndromes that interfere with insulin secretion (e.g., pheochromocytoma) or cause peripheral insulin resistance (e.g., acromegaly, Cushing syndrome, pheochromocytoma), and drug-induced diabetes (e.g., phenytoin, glucocorticoids, estrogens).

Diabetes mellitus is characterized by inappropriate regulation of serum glucose levels. In Type 1 diabetes an autoimmune attack on the endocrine pancreas results in progressive and irreversible destruction of the insulin secreting beta cells. Loss of insulin action on insulin-sensitive target cell glucose uptake and metabolism results. Type 2 diabetes has several etiologies, most often reflected in cellular resistance to insulin action, also with attendant alterations in the regulation of serum glucose levels. Insulin acts through a disulfide-bonded heterotetrameric cell surface receptor comprised of an extracellular alpha subunit coupled via disulfide bonds to a transmembrane and intracellular beta subunit. In Type 1 diabetes, absence of the ligand with normal cellular receptor structure and function is most often the cause of the subsequent metabolic defects. Hormone replacement therapy in the form of daily insulin injections supplies the ligand for receptor action, though not necessarily in a normal physiologic fashion. In Type 2 diabetes, resistance to the action of insulin often underlies the disease with some of the resistance due to defects in receptor action.

It is known in case of insulin resistance that a higher amount of insulin is required to set on the insulin signaling cascade by the insulin receptor. The present invention is related to a cell membrane protein of adipocytes which is able to stimulate glucose uptake by circumventing the insulin receptor triggered signaling pathway. This provides for a powerful solution of the problem not to have in hands a screening tool to identify compounds which could act as alternatives for insulin.

SUMMARY OF THE INVENTION

Therefore the present invention refers to a protein from the plasma membrane of an adipocyte which is possibly stabilized by simultaneous presence of plasma membranes and/or lipid vesicles and/or raft domains with high cholesterol and/or lipid vesicles and which has specific binding affinity to phosphoinositolglycan or a phosphoinositolglycan-peptide characterized by a) ability to trigger tyr phosphorylation of insulin receptor substrate 1 or 2 in an adipocyte after specific binding of a phosphoinositolglycan or a phosphoinositolglycan-peptide to this protein and b) ability to stimulate glucose uptake in an adipocyte after specific binding of a phosphoinositolglycan or a phosphoinositolglycan-peptide to this protein.

The amount of the protein with respect to other proteins and/or the stabilizing components and/or other compounds (e.g. salts, ion, puffer) is in a range between 0.01 to 10%, or about 0.01 to 10%, with respect to the wet weight.

The amount of the protein is preferably in a range of 0.1 to 5%, or about 0.1 to 5% with respect to the wet weight and most preferably in a range of 0.1 to 1%, or about 0.1 to 1% with respect to the wet weight.

Under native conditions the amount of the said protein in plasma membranes is in the range of less than $10^{-6}$% with respect to the wet weight.

In preferred modifications of the invention the phosphoinositolglycan or phosphoinositolglycan-peptide consists at least of one compound of the following: YCN-PIG, YMN-PIG, PIG37, YCN or IcGce1.

The binding of the phosphoinositolglycan or phosphoinositolglycan-peptide to the protein takes place preferably with a binding constant ($K_D$) of 0.001 to 10 μM, or about 0.001 to 10 μM.

The binding constant is a thermodynamic order for quantitative description of the equilibrium between the dissociated and non-dissociated forms of the complexes between the protein and the phosphoinositolglycan or phosphoinositolglycan-peptide.

The binding constant is formed by the quotient of the velocity constants of forward and backward reaction. High values of the binding constant (e.g. larger than 10 mM) define a weak and unspecific binding whereas low values (e.g. not more than 100 μM) define a strong and specific binding.

The binding constants can be determined by different methods as for example by equilibrium dialysis, spectroscopy or graphical approaches (Scatchard-Plot).

The adipocyte plasma membrane referring to is preferably from a rat, mouse or human.

The molecular weight of the protein is between 100 to 120 kDa, preferably between 110 to 120 and most preferably of 115 kDa. It must be mentioned that determination of molecular weight of proteins by any method in particular by SDS-PAGE occurs with an uncertainty of ±5 to 10%.

The invention further relates to a complex which is formed by the protein of the invention as aforementioned and by at least one compound of the following group: YCN-PIG, YMN-PIG, PIG37, YCN or IcGce1.

Prerequisite of complex formation is specific binding of the ligand to the protein. The complex may be stabilized by forming of an ionic or covalent bondage between ligand and protein.

The invention refers also to the production of a protein of the invention wherein a) adipocytes will be provided from a rat, mouse or human tissue, b) the plasma membranes of the adipocytes from a) will be isolated, c) raft domains with high cholesterol (hcDIGs) are prepared from plasma membranes of b)

d) the hcDIGs from c) are treated with a trypsin/NaCl solution, e) the incubation mixture from d) is centrifuged and the proteins of the supernatant are separated by means of SDS-PAGE Sodium-Dodecylsulfate-Polyacrylamidegel-electrophoresis, f) the protein fraction with size of 100 to 120 kDa, or about 100 to about 120 kDa is eluted from the gel and possibly solubilized by a solution or suspension containing a detergent or biological membranes.

Furthermore the invention refers to a method for identifying a compound which specifically binds to a protein of the invention wherein a) a fraction of a cell is provided, which contains a protein of the invention, b) a compound is provided, c) the fraction of the cell from a) is brought in contact with the compound of b), d) binding of the compound to the fraction of a cell from a) is determined, e) specificity of binding is deduced by comparison of results from d) with results from an experiment in which the same compound as from b) is brought in contact with a fraction of a cell which has the same species and/or tissue specificity as the cell from a) but does not contain a protein of the invention thereby indicating a higher specificity of binding in case a higher amount of the compound from b) is binding to the fraction of the cell which contains the protein of the invention than to the fraction of the cell which does not contain the protein of the invention.

The fraction of the cell is taken preferably from an adipocyte, a skeletal muscle cell, a heart muscle cell or a liver cell. Each of these cells can be derived preferably from a mouse, rat or a human. The fraction of the cell consists preferably of cell membranes of a cell or more preferably of raft domains of high cholesterol content (hcDIGs). The compound which is used for performing the method for identifying a compound which specifically binds to a protein of the invention can be labeled with a radioactive nuclide (e.g. $^{14}$C, $^{3}$H, $^{32}$P, $^{121}$J and others) or a fluorescence marker.

The invention refers further to a method for identifying a compound which specifically binds to a protein of the invention wherein
a) a glucose transporting cell is provided which contains a protein of the invention,
b) a compound is provided,
c) the cell from a) is brought in contact with the compound of b)
d) binding of the compound to the glucose transporting cell is determined,
e) the specificity if binding is deduced by comparison of results from d) with results from an experiment in which the same compound as from b) is brought in contact with a glucose transporting cell which has the same species and/or tissue specificity as the cell from a) but does not contain a protein of the invention thereby indicating a higher specificity of binding in case a higher amount of the compound from b) is binding to the glucose transporting cell which contains a protein of the invention than to the glucose transporting cell which does not contain the protein of the invention.

A glucose transporting cell which does not contain a protein of the invention can be produced from a glucose transporting cell which contains a protein of the invention by treating this cell which contains the protein of the invention with a trypsin/NaCl solution and/or a glycosidase.

The glucose transporting cell is preferably an adipocyte, a skeletal muscle cell, a heart muscle cell or a liver cell. These cells are preferably taken from a tissue or cell culture of human, mouse or human origin.

The compound used is preferably labeled with a radioactive nuclide or a fluorescence marker.

Furthermore the invention refers to a method for identifying a compound which is an agonist or antagonist for a protein of the invention wherein
a) a glucose transporting cell is provided, wherein the protein of the invention is present,
b) a natural ligand of the protein of the invention is provided,
c) a chemical compound is provided,
d) the glucose transporting cell of a) is brought into contact with the ligand from b) and the chemical compound from c),
e) the glucose uptake of the glucose transporting cell from d) is determined,
f) the glucose uptake of the glucose transporting cell from d) is determined wherein stimulation of glucose uptake means agonistic activity and inhibition of glucose uptake means antagonistic activity of the compound from c).

The ligand of the aforementioned method for identifying an agonist or antagonist of the protein of the invention is preferably YCN-PIG, YMN-PIG, PIG37, YCN or IcGce1.

The glucose transporting cell of the method for identifying an agonist or antagonist of the protein of the invention is preferably an adipocyte, a skeletal muscle cell, a heart cell or a liver cell and is preferably of human, mouse or rat species origin.

The invention refers also to a medicament containing a compound which has been identified by a method of identifying a compound which binds to a protein of the invention or which is a agonist or antagonist of the protein of the invention as well as auxiliary compounds for formulation of a medicament. The medicament contains in preferable embodiments at least of one compound of the following group: YCN-PIG, YMN-PIG. PIG37, YCN or IcGce1.

The medicament could also contain a part or derivative of at least one compound of the following group: YCN-PIG, YMN-PIG, PIG37, YCN or IcGce1.

Furthermore the invention refers to use of a compound which has been identified to bind to the protein of the invention or to be an agonist or antagonist of the protein of the invention for production of a medicament for treatment of insulin resistance or diabetes.

Such compound could preferably be YCN-PIG, YMN-PIG, PIG37, YCN, IcGce1 or a part or derivative of one of these compounds.

DETAILED DESCRIPTION OF THE PREFERRED EMBODIMENTS

Figure 1:
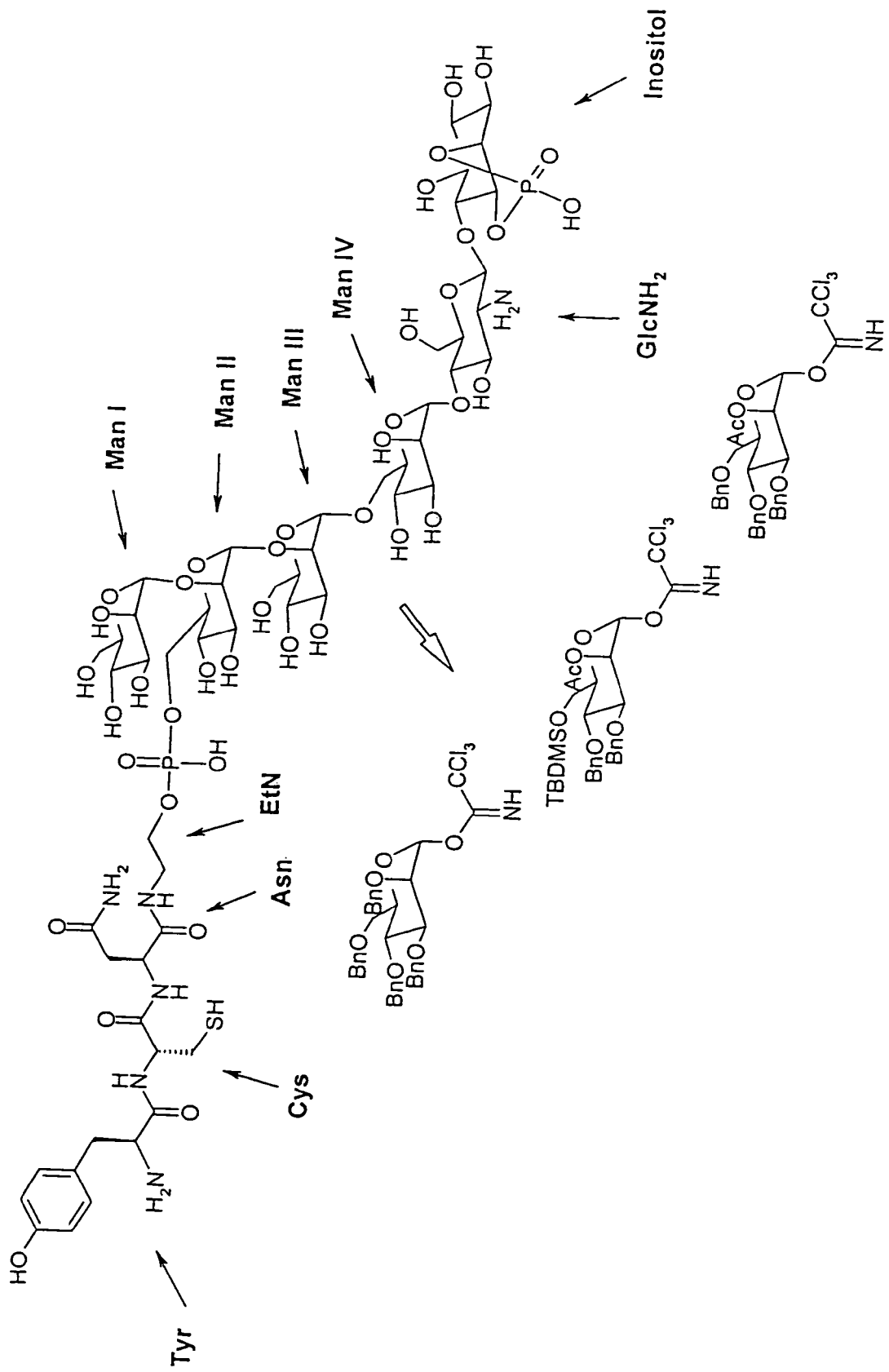
FIG. 1: General scheme of synthesis of PIG, part 1.

In a preferred embodiment, the invention provides a method of identifying a protein from a plasma membrane of an adipocyte comprising providing adipocytes from a mammal, isolating plasma membranes from said adipocytes, isolating domains with high cholesterol (hcDIGs) from the plasma membranes, isolating a protein fraction with size of about 115 kDa from said domains. The step of isolating a protein fraction with size of about 115 kDa further comprises solubilizing the fraction in a solution or suspension comprising a detergent or biological membranes. The solution or suspension further comprises one or more compounds selected from YCN-PIG, YMN-PIG, PIG37, YCN or IcGce1. The protein has specific binding affinity to phosphoinositolglycan or a phosphoinositolglycan-peptide. The phosphoinositolglycan or phosphoinositolglycan-peptide binds to the protein with a binding constant of between 0.001 to 10 μM.8. The adipocyte is preferably from rat, mouse or human origin. The molecular weight of the protein is about 100-150 kDa, preferably about 115 kDa.

In another preferred embodiment, the invention provides a method for identifying a compound which specifically binds to a protein with specific binding affinity to phosphoinositoylglycans comprising contacting a fraction of a cell with a compound, and determining if said compound binds with said protein. The method preferably further comprises the step of determining specificity of binding. This may be done by comparing binding of the compound to the fraction with results from an experiment of bringing said compound in contact with another fraction of a cell which has the same species and/or tissue specificity as the first fraction but does not comprise said protein; wherein a higher amount of the compound binding to the fraction of the cell which contains said protein indicates specificity of said compound for said protein. The fraction preferably comprises domains of high cholesterol content (hcDIGs). Preferably, the compound is labeled with a radioactive nuclide or a fluorescence marker.

In another preferred embodiment, the invention also provides a method for identifying a compound which specifically binds to a protein with specific binding affinity to phosphoinositoylglycans, wherein said cell is from a glucose transporting cell, comprising contacting a fraction of the cell with a compound and determining if said compound binds with said protein. The method also further comprises the step of determining specificity of binding, wherein said step comprises comparing a binding of the compound to the fraction with results from an experiment comprising bringing said compound in contact with a fraction of a cell which has the same species and/or tissue specificity as the first fraction but does not comprise said protein; wherein a higher amount of the compound binding to the fraction of the cell which contains said protein indicates specificity of said compound for said protein. The compound is preferably labeled with a radioactive nuclide or a fluorescence marker.

In another preferred embodiment, the invention also provides a method for identifying a compound which is an agonist or antagonist for a protein with specific binding affinity to phosphoinositoylglycans, comprising bringing a glucose transporting cell into contact with a natural ligand of the protein and a chemical compound, and determining glucose uptake of the glucose transporting cell, wherein stimulation of glucose uptake indicates that the compound is an agonist and inhibition of glucose uptake indicates he compound is an antagonist. Preferably, the natural ligand is selected from YCN-PIG, YMN-PIG, PIG37, YCN or IcGce1. The cells are of mammalian cells, preferably human, mouse or rat species origin.

EXAMPLES

Chemical Synthesis of PIG(-P): Synthesis of YCN-PIG (for the general strategy, see FIGS. 1, 2, 3)

For synthesis of product 2 (FIG. 4; i, ii), product 1 (8.0 g, 20.6 mmol) from Bachem (Heidelberg, Germany) was dissolved in 200 ml of pyridine, and 5 g (81.8 mmol) of ethanolamine and 5 ml of N-ethylmorpholine were added. After standing (16 h, room temperature), 50 ml of acetic anhydride were added dropwise at 5° C., with stirring. The reaction mixture was stirred (2 h, room temperature) and then concentrated under high vacuum. The residue was dissolved in 150 ml of hot methanol and the solution was concentrated. The product crystallizes after the addition of 100 ml of methylene chloride/methanol (15/1) and 200 ml of n-heptane/ethyl acetate (2/1). Yield of product 2: 6.1 g (84%) of white crystals of m.p. 175° C. TLC (Thin Layer Chromatography): methylene chloride/methanol (9/1), $R_f$=0.7. MS: $(M+Li)^+$=358.2, calculated $C_{16}H_{21}N_3O_6$, M=351.36.

For synthesis of product 3 (FIG. 4; iii), 2.0 g of palladium-on-charcoal (10% Pd) was added to a solution of Product 2 (12.0 g, 34.0 mmol) in 200 ml of methanol/acetic acid (1/1) and the mixture was hydrogenated (2 h, room temperature). The solution was filtered on silica gel and concentrated and the residue purified by flash chromatography (methylene chloride/methanol/concentrated ammonia 30/5/1). Yield of product 3: 7.3 g (98%) of a yellowish oil. TLC: methylene chloride/methanol/concentrated ammonia (30/5/1), $R_f$=0.5. MS: $(M+Li)^+$=224.2, calculated $C_8H_{15}N_3O_4$, M=217.23.

For synthesis of product 4 (FIG. 4; iv), 1.5 g (4.5 mmol) of 1(o-(cyano(ethoxycarbonyl)-methyliden)amino-1,1,3,3-tetramethyluronium tetrafluoroborate (TOTU), 0.64 g (4.5 mmol) of ethyl-(hydroxyimino)-cyanoacetate (oxime) and 1.7 ml (13.5 mmol) of N-ethylmorpholine were added at 0° C., with stirring, to a solution of 0.8 g (3.7 mmol) of 3 and 2.8 g (4.5 mmol) of TrtCys(Trt)OH in dimethylformamide and the mixture was stirred (2 h, 0° C.). After the addition of 200 ml of ethyl acetate, the mixture was washed 3 times with saturated $NaHCO_3$ solution, dried over $MgSO_4$ and concentrated. The residue was triturated with n-heptan/ethyl acetate (6/1) and the product crystallizes. Yield of product 4: 2.2 g (74%) of white crystals of m.p. 185° C. TLC: methylene chloride/methanol (15/1), $R_f$=0.4. MS: $(M+Li)^+$=811.7, calculated $C_{49}H_{48}N_4O_5S$, M=805.0.

For synthesis of product 6 (FIG. 4; v, vi), 4.0 g (5.0 mmol) of product 4 was dissolved in 200 ml of methylene chloride. 4 ml of water and 3 ml of trifluoroacetic acid was added. After 15 min, the mixture was washed 3 times with saturated $NaHCO_3$ solution, dried over $MgSO_4$ and concentrated, to yield 99% crude product 5. This crude product was dissolved in 50 ml of methanol, and 0.5 ml of 1 M sodium methanolate solution was added dropwise. After 15 min, 50 ml of methylene chloride were added and the mixture was filtrated on silica gel. After concentration of the solvent, the residue was purified by flash chromatography (methylene chloride/methanol (9/1)). Yield of product 6: 2.2 g (85%) of a white amorphous solid. TLC: methylene chloride/methanol (5/1), $R_f$=0.7. MS: $(M+Li)^+$=527.3, calculated $C_{28}H_{32}N_4O_4S$, M=520.6.

For synthesis of product 7 (FIG. 4; vii), 2.7 g (5.2 mmol) of product 6, 4.2 g (10.4 mmol) of Ztyr(Bn)OH, 3.4 g (10.4 mmol) of TOTU, 1.5 g (10.4 mmol) of oxime and 2 ml of N-ethylmorpholine in 50 ml dimethylformamide were reacted analogously to the preparation of product 4. Yield of product 7: 4.2 g (89%) of white crystals. TLC: methylene chloride/methanol (15/1), $R_f$=0.25. MS: $(M+Li)^+$=914.8, calculated $C_{25}H_{53}N_5O_8S$, M=908.1.

For synthesis of product 8 (FIG. 5; viii), 6.0 g (73 mmol) of phosphorous acid was concentrated four times with pyridine and then taken up in 180 ml of dry pyridine. 13 ml of pivaloyl chloride were added dropwise at 10° C. This reaction solution was allowed to stand (45 min, room temperature). 16.4 g (18.1 mmol) of product 7 was introduced into the reaction solution as described above. After 5 h, it was diluted with 200 ml of toluene and 150 ml of methylene chloride/methanol/33% $NH_3$ (30/10/3). After concentration residual pyridine was distilled out a further three times with 200 ml toluene. The residue was suspended in 200 ml of methylene chloride/methanol (20/1). The non-soluble constituents were filtered and washed twice with 50 ml of methylene chloride/methanol (20/1). The filtrate was concentrated and purified by flash chromatography. Yield of product 8: 11.6 g (66%) of white crystals. TLC: methylene chloride/methanol/33% $NH_3$ (30/5/1), $R_f$=0.25. MS: $(M+Li)^+$=978.4, calculated $C_{52}H_{54}N_5O_{10}SP$, M=972.08.

For synthesis of product 10 (FIG. 6; ix, x), 4.5 g of product 8 (4.6 mmol) and 6.0 g of product 9 (2.3 mmol; synthesis performed as described previously in ref. 47) were dissolved in 80 ml dry pyridine. After 30 min at room temperature, the reaction was cooled to 0° C. and 5 ml water and 1.3 g iodine was added. The reaction mixture was stirred (30 min, 10° C.) and then diluted with 500 ml methylene chloride, 150 ml of saturated NaCl solution and 30 ml of saturated thiosulfate solution and stirred for 5 min. The organic phase was dried over $MgSO_4$ and concentrated. The residue was purified by flash chromatography with methylene chloride/methanol/conc. $NH_3$ (30/5/1 to 30/10/3). Yield of product 10: 8.0 g as amorphous solid. TLC: methylene chloride/methanol (20/1), $R_f$=0.5. MS: $(M+Li)^+$=3583.6, calculated $C_{207}H_{214}N_8O_{42}SP_2$, M=3580.0.

For synthesis of product 11 (FIG. 6; xi), 300 ml of ammonia were condensed at −78° C. 2.1 g (91 mmol) of sodium was dissolved therein. This solution was diluted with 150 ml of dry tetrahydrofurane and 8.0 g of product 10 (2.2 mmol) of the protected final product dissolved in 50 ml of dry tetrahydrofurane were then slowly added dropwise at a reaction temperature of −78° C. After a reaction time of 15 min (blue color must not disappear), the mixture was treated cautiously with 5 g of ammonium chloride. When the blue color had disappeared, the mixture was diluted cautiously with 50 ml of water and 150 ml of methanol. It was allowed to thaw and then concentrated to about 100 ml. This solution was diluted with 500 ml of methylene chloride/methanol/33% $NH_3$ (3/3/1) and added to a flash silica gel column (500 ml of silica gel). It was eluted sequentially with 1 l each of methylene chloride/methanol/33% $NH_3$ (3/3/2) and (3/3.5/3). The product eluted was then chromatographed using n-butanol/ethanol/water/33% $NH_3$ (2/2/2/1). Yield of product 11: 2.4 g (67% from product 9) as a white solid. TLC: n-butanol/ethanol/water/33% $NH_3$ (2/2/2/1), $R_f$=0.5. MS: $(M+NH_3)^+$=1572.6; calculated $C_{54}H_{88}N_6O_{40}P_2S$, M=1555.31. $^{31}$P-NMR $(D_2O)$=15.3 ppm for cyclic phosphate and 0.3 for phosphordiester. The data from $^1$H- and $^{13}$C-NMR are shown in Table 1.

For synthesis of product YCN (FIG. 7; xii), 11.0 g (11.3 mmol) of product 7 was deprotected analogously to the preparation of product 11. Yield of YCN: 4.5 g (90%) of white crystals. TLC: methylene chloride/methanol/concentrated ammonia (30/15/5), $R_f$=0.25. MS: $(M+Li)^+$=448.3, calculated $C_{18}H_{27}N_5O_6S$, M=441.51.

Figure 2:
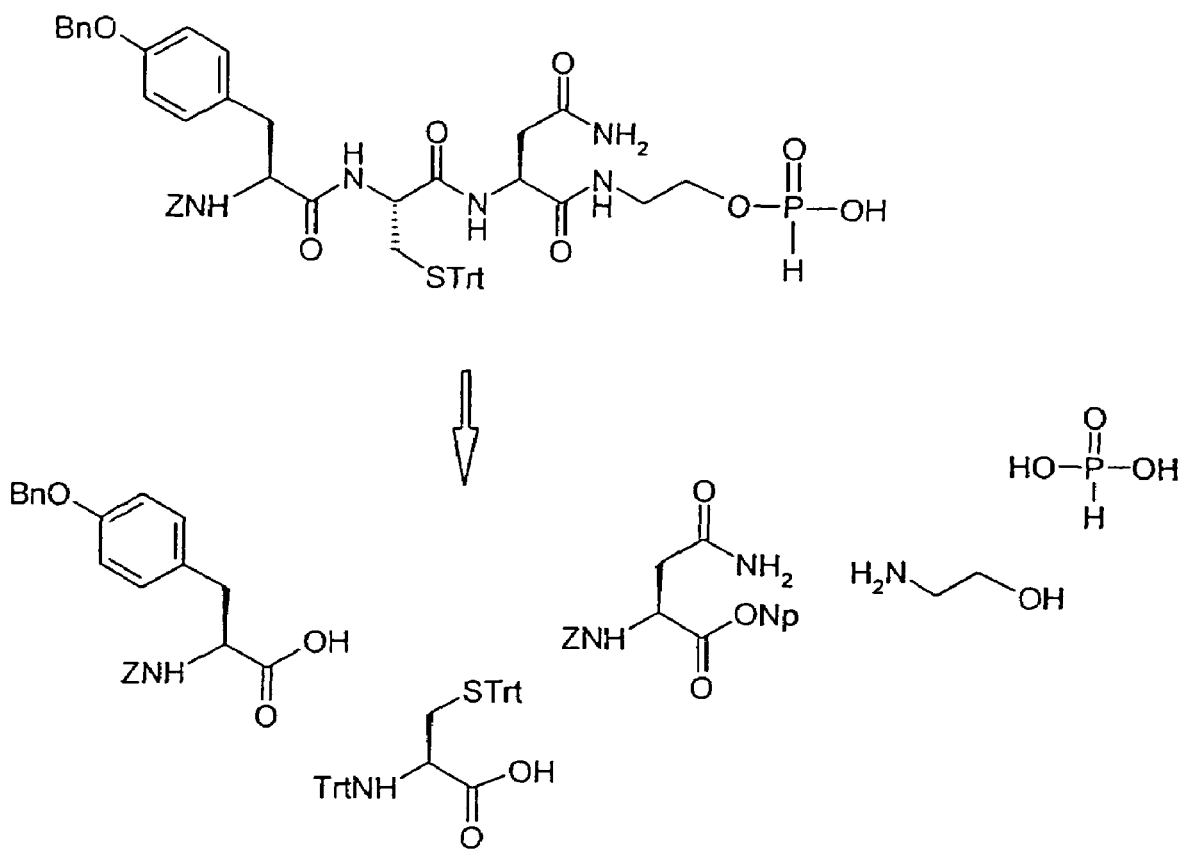
FIG. 2: General scheme of synthesis of PIG, part 2.

For synthesis of product YMN-PIG, YMN-PIG was synthesized with the same reaction sequence as shown in FIG. 2. The use of BocMetOH instead of TrtCys(Trt)OH resulted in YMN-PIG in similar yields as a white solid. TLC: n-butanol/ethanol/water/33% $NH_3$ (2/2/2/1), $R_f$=0,5. MS: $(M+NH_3)^+$=1600.6; calculated $C_{56}H_{92}N_6O_{40}P_2S$, M=1583.38. $^{31}$P-NMR $(D_2O)$=15.3 ppm for cyclic phosphate and 0.3 for phosphordiester.

Preparation of Radiolabeled and Lipolytically Cleaved Gce1p (IcGce1p)

Gce1p with intact GPI anchor was purified from lactate-grown yeast cells which had been metabolically labeled with myo-[$^{14}$C]inositol and then enzymatically converted to spheroplasts. Plasma membranes were prepared, purified by Ficoll gradient centrifugation, solubilized using 0.35% β-amidotaurocholate and subjected to TX-114 partitioning. Gce1p contained in the detergent-enriched phase was purified by gel filtration chromatography on Sephadex S-300, affinity chromatography on $N^6$-(2-aminoethyl)-cAMP Sepharose and phenyl Sepharose chromatography. Elution from the columns was followed by on-line monitoring of $^3$H-radioactivity. Partially purified Gce1p was precipitated (12% polyethylene glycol 6000), then resuspended in buffer G (25 mM Tris/acetate, pH 7.4, 144 mM NaCl, 0.1% β-amidotaurocholate, 0.5 mM DTT, 0.2 mM EDTA, 5% glycerol, 0.1 mM PMSF, 5 μM leupeptin, 1 mM iodoacetamide, 10 μg/ml soy bean trypsin inhibitor) at 0.2 mg protein/ml and subsequently incubated (3 h, 25° C.) in the presence of 6 U/ml PI-specific PLC (*B. cereus*). After addition of 10 volumes of an ice-cold solution of 2% Triton X-114, 10 mM Tris/HCl (pH 7.4), 144 mM NaCl and phase separation (incubation for 2 min at 37° C. and centrifugation at 12,000×g for 1 min at 25° C.), IcGce1p was recovered from the upper detergent-depleted phase. After two reextractions of the lower detergent-enriched phase by addition of an equal volume of 10 mM Tris/HCl, 144 mM NaCl, redissolvation on ice and subsequent phase separation, the combined detergent-depleted phases were precipitated (12% polyethylene glycol 6000).

Radiolabeled IcGce1p was supended in buffer lacking β-amidotaurocholate at 200-1000 dpm/μl.

Preparation of Radiolabeled YCN-PIG

Radiolabeled YCN-PIG was derived from Gce1p by sequential digestion with V8 protease (*S. aureus*) and PI-PLC (*B. cereus*). YCN-PIG was recovered from the detergent-depleted phase after TX-114 partitioning and then sequentially purified by cation exchange chromatography (Dowex 50W-X8), gel filtration on BioGel-P4, anion change chromatography on SAX HPLC column, two thin layer chromatographic runs on Si-60 HPTLC plates using different solvent systems and a final gel filtration on BioGel-P4. The elution of material during each chromatographic separation was followed by measurement of $^3$H-radioactivity, UV absorption $(A_{220})$ and insulin-mimetic activity according to stimulation of glucose transport in isolated rat adipocytes. For demonstration of radiochemical purity, the final preparation of YCN-PIG was subjected to Dionex CarboPac PA-1 anion exchange HPLC at pH 13 calibrated in Dionex units by inclusion of a glucose oligomer standard mix. The internal standards were detected using a pulsed amperiometric detector. The $^{14}$C-labeled fragments were followed by the Raytest Ramona on-line radioactivity monitor. For determination of the concentration, YCN-PIG were hydrolyzed (6 M HCl, 16 h, 110° C.) and the amount of inorganic phosphate (2 mol/molecule) and tyrosine (1 mol/molecule) was determined. Dried YCN-PIG was stored at −80° C. until use and then suspended in $H_2O$ containing 2 mM DTT at a final concentration of 100 μM.

Preparation of Rat Adipocytes and Incubation with PIG(-P)/YCN

Adipocytes were isolated by collagenase digestion from epididymal fat pads of male Sprague Dawley rats (140-160 g, fed ad libitum) and incubated in KRH buffer (0.14 mM NaCl, 4.7 mM KCl, 2.5 mM $CaCl_2$, 1.2 mM $MgSO_4$, 1.2 mM $KH_2PO_4$, 20 mM Hepes/KOH, pH 7.4) containing 1% (w/v) BSA, 100 μg/ml gentamycin, 100 mM 1-methyl-2-phenylethyladenosine, 0.5 U/ml adenosine deaminase, 0.5 mM sodium pyruvate and 5 mM D-glucose in the presence of PIG(-P)/YCN (dissolved in 20 mM Hepes/KOH, pH 7.4, 2 mM DTT) at 37° C. in a shaking water bath at constant bubbling with 5% $CO_2$/95% $O_2$ for the periods indicated.

Treatment of Rat Adipocytes with Trypsin/NaCl or NEM

For trypsin/NaCl-treatment, 2 ml of adipocyte suspension ($3.5 \times 10^6$ cells/ml) in KRH containing 5 mM glucose was incubated (20 min, 30° C.) in the presence of 100 μg/ml trypsin. Soy bean trypsin inhibitor (final conc. 100 μg/ml) and 2 ml of KRH containing 1 M NaCl and 0.5% BSA were added and the incubation (10 min, 22° C.) continued. For NEM-treatment, 1 ml of adipocyte suspension ($3.5 \times 10^6$ cells/ml) in KRH containing 5 mM glucose was incubated (30 min, 25° C.) with NEM (1.5 mM final conc.) and then with DTT (15 mM final conc., 5 min). After the treatments, the cells were centrifuged (1500×g, 5 min, swing-out rotor) and the infranatant removed by suction. The cell suspension left (about 0.5 ml) was supplemented with 10 ml of KRH containing 0.5% BSA and then centrifuged again (500×g, 1 min, swing-out rotor). After two additional washing steps, the final cell suspension was adjusted to 25 ml of KRH containing 0.5% BSA, 50 µM glucose and 1 mM sodium pyruvate. 0.2 ml portions were assayed for lipigenesis to monitor the loss of responsiveness toward PIG41. Control cells were subjected to the same centrifugation and washing procedures as the treated cells with $H_2O$ replacing trypsin/NaCl. For radiolabeling of adipocytes with [$^{14}C$]NEM, the cell suspension was centrifuged (500×g, 1 min) and the infranatant removed. 50-µl portions ($7 \times 10^6$ cells/ml) were incubated (10 min, 30° C.) with 2.5 µCi[$^{14}C$]NEM in a total volume of 60 µl. After addition of 5 µl of 10 mM DTT and 55 µl of KRH containing 10 mM glucose, the trypsin/NaCl-treatment was performed as described above in a total volume of 200 µl. 50-µl portions were carefully layered over 200-µl oil layers consisting of dinonyl phthalate in 0.4-ml centrifugation tubes. After centrifugation (5,000×g, 15 sec), the tubes were cut through the oil layer. Proteins of the medium contained in the lower part of the tubes were precipitated (10% TCA, two acetone washes), suspended in Laemmli sample buffer and analyzed by SDS-PAGE.

Preparation of Plasma Membranes, Total Cell Lysates and Micosomes

Postnuclear infranatant was prepared from isolated rat adipocytes as described previously. For preparation of plasma membranes, 1 ml portions were layered on top of 5 ml cushions of 38% (w/v) sucrose, 25 mM Tris/HCl (pH 7.4), 1 mM EDTA, and centrifuged (110,000×g, 1 h). The membranes at the interface between the two layers (0.5 ml) were removed by suction, diluted with four volumes of homogenization butter, and layered on top of an 8 ml cushion of 28% Percoll, 0.25 M sucrose, 1 mM EDTA, 25 mM Tris/HCl (pH 7.0). After centrifugation (45,000×g, 30 min), the plasma membranes were withdrawn from the lower third of the gradient (0.5 ml) with a Pasteur pipette, diluted with 10 volumes of homogenization buffer and centrifuged (200,000×g, 90 min). For binding studies, the washed pellet was suspended in binding buffer at 1-2 mg protein/ml. For preparation of total cell lysates, the postnuclear infranatant was supplemented with deoxycholate and Nonidet P-40 (final conc. 0.3 and 0.2%, respectively), incubated (1 h, 4° C.) and finally centrifuged (100,000×g, 1 h, 4° C.). The supernatant was used for immunoprecipitation. For preparation of microsomes, the postnuclear supernatant was centrifuged (100,000×g, 1 h, 4° C.). The pellet was suspended in binding buffer at 1-2 mg protein/ml.

Preparation of hcDIGs/IcDIGs

Purified pelleted plasma membranes (0.5-1 mg) were suspended in 1.5 ml of ice-cold 0.5 M $Na_2CO_3$ (pH 11) containing 50 mM NaF, 5 mM sodium pyrophosphate, 10 µM okadaic acid, 1 mM sodium orthovanadate, 20 µM leupeptin, 5 µM pepstatin, 1 µM aprotinin, 5 mM iodoacetate, 200 µM PMSF, 1 mM EDTA and incubated (1 h, 4° C. under repeated vortexing and suction with a pipette). The suspension was then mixed with an equal volume of 85% sucrose in 15 mM MES/KOH (pH 6.5), 75 mM NaCl and overlaid with 1.5 ml cushions each of 42.5, 35, 28, 22, 15 and 5% sucrose in the same medium, and centrifuged (230,000×g, Beckman SW41 rotor, 18 h). The light-scattering opalescent bands of flocculent material at the 15-22% (fractions 4 and 5) and 28-35% (fractions 8 and 9) sucrose interfaces as well as the material of the 42.5% cushions (fractions 12-15) were collected as hcDIGs, IcDIGs and solubilized plasma membrane proteins, respectively, using a 19-gauge needle and a syringe (0.75 ml per fraction). Density was determined by measuring the refractive index of the fractions. hc/IcDIGs were characterized by enrichment/deprivation of relevant markers as described previously. For binding studies, hc/IcDIGs were suspended in binding buffer (15 mM Mes/KOH, pH 6.5, 0.25 M sucrose, 75 mM NaCl, 2 mM $MgCl_2$, 0.5 mM EDTA, 0.5 mM DTT, protease inhibitors).

Binding of Radiolabeled YCN-PIG or IcGce1p to Subcellular Fractions

10 µl, of radiolabeled YCN-PIG or IcGce1p (60,000-80,000 dpm/nmol, final conc. 5 µM) was added to 40 µl of suspended plasma membranes, microsomes or hc/IcDIGs (40-80 µg of protein) in binding buffer in the absence or presence of unlabeled competitor (as indicated in the figure legends) in a total volume of 100 µl and incubated (30 min, 4° C.). For separation of membranes from the incubation medium, 45 µl aliquots were carefully layered over 200 µl, oil layers consisting of dibutyl phthalate and dioctyl phthalate (1/1 by vol., final density 1.012) in case of plasma membranes/microsomes or dibutyl phthalate and dinonyl phthalate (1/9 by vol., final density 9.863) in case of hc/IcDIGs in 0.4 ml precooled (4° C.) centrifugation tubes (microtubes no. 72.700, Sarstedt, Germany). After centrifugation (48,000×g, 2 min), the tubes with caps closed were cut through the oil layer and the lower and upper parts of the tubes (with caps removed) containing the pelleted plasma membranes/microsomes and the floating hc/IcDIGs, which did or did not penetrate the oil layer, respectively, transferred into 10 ml scintillation vials containing 1 ml of 10% SDS. After rigorous shaking (16 h, 25° C.), the radioactivity was counted in 9 ml of ACSII scintillation cocktail (Beckman). Under these conditions, sticking to the tube walls and partitioning into the oil layer of both radiolabeled YCN-PIG and IcGce1p accounted for 50-120 dpm (i.e. less than 0.5% of total radioactivity used per incubation) and therefore was not considered for calculation of binding data. Typical recoveries of plasma membranes and microsomes were 78-85% and 65-80%, respectively, and of hcDIGs and IcDIGs 83-92% and 70-78%, respectively, according to protein determination.

Chemical Synthesis of PIG(-P)

Figure 3:
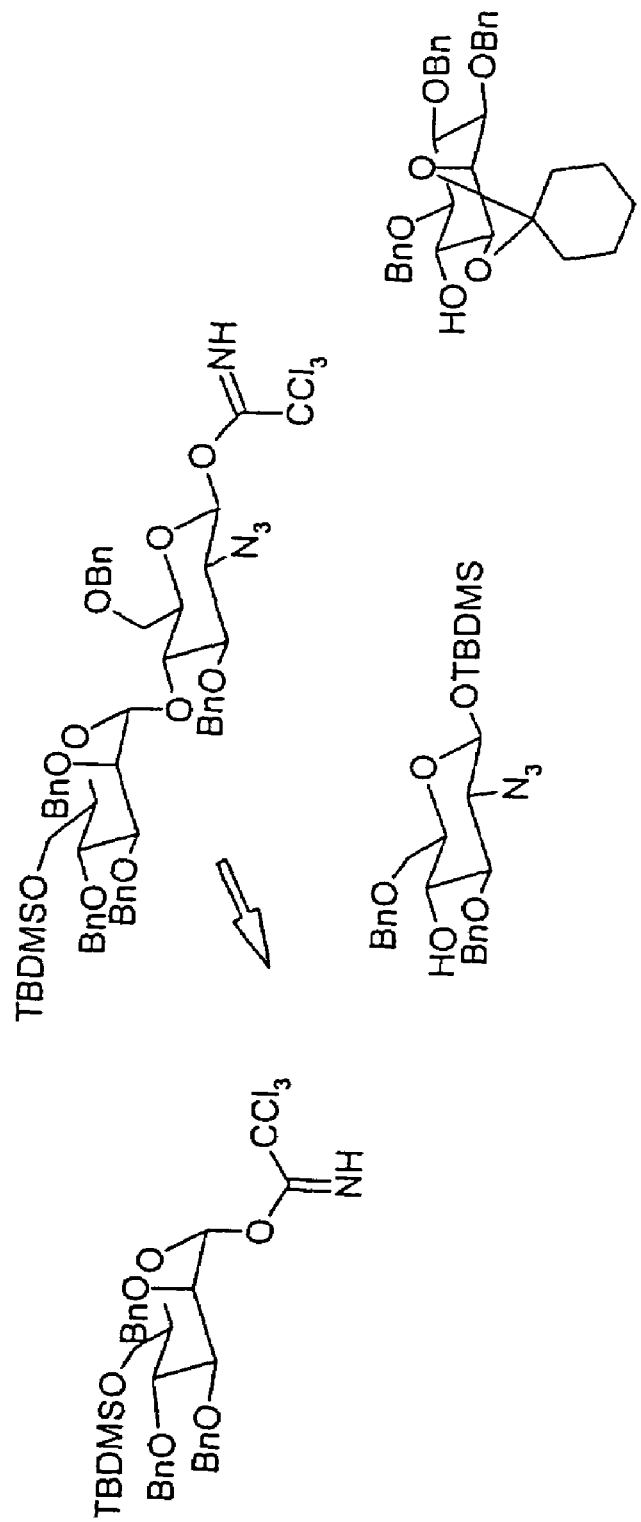
FIG. 3: General scheme of synthesis of PIG, part 3.
Figure 4:
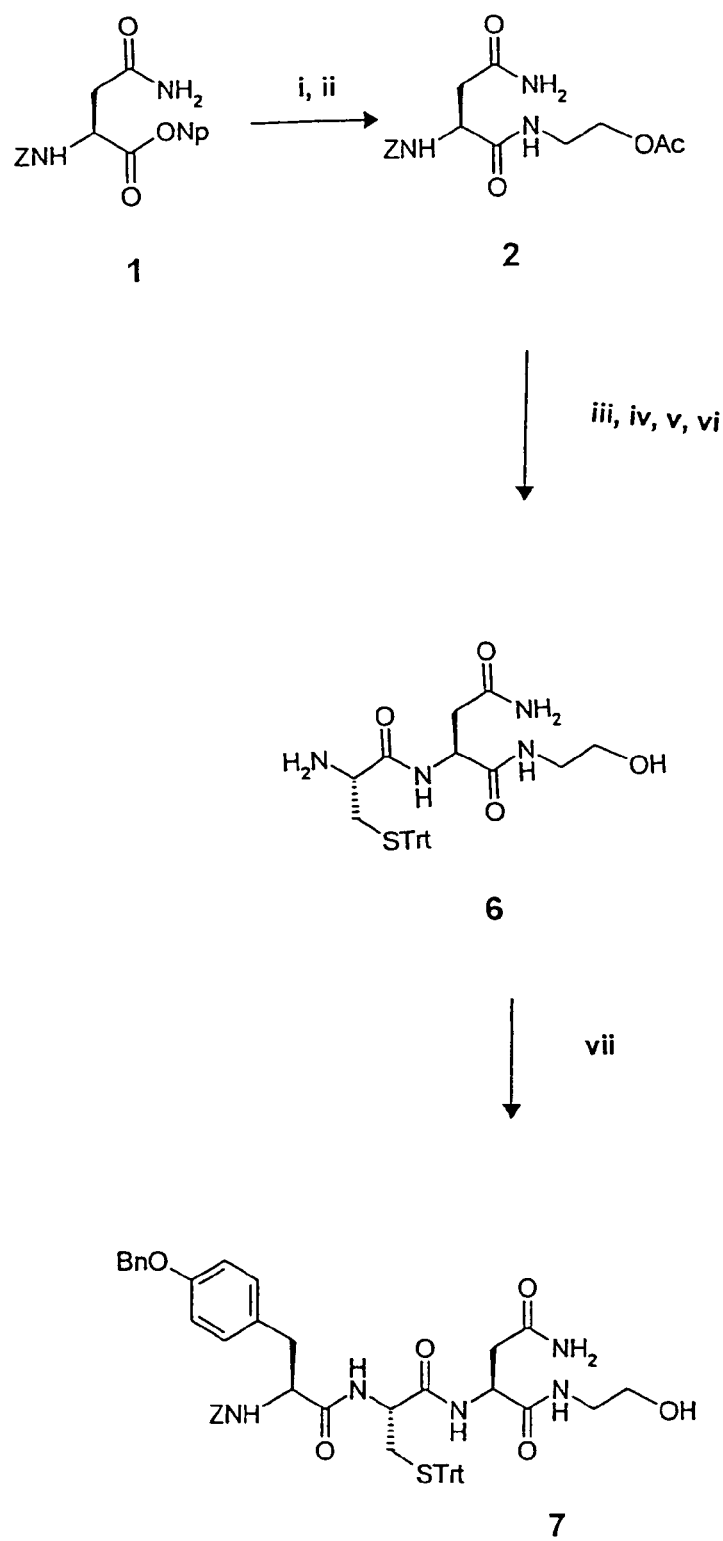
FIG. 4: Synthesis of YCN-PIG, part 1.

Hydrophilic GPI structures can be generated from natural sources by two experimental approaches: (i) PIG released by GPI-specific PLC/D from free GPI lipids as their polar core glycan head groups and therefore lacking any amino acids and (ii) PIG-P generated by combined lipolytic and proteolytic cleavages from a GPI protein yielding the polar core glycan head group together with one to several amino acids derived from the carboxy-terminus of the GPI protein left. Both GPI lipids and GPI proteins reside in the outer leaflet of the plasma membrane of eucaryotic cells with the core glycan head groups conserved from yeast to man. For assaying binding of the GPI core glycan head group, the disclosure of synthesis of a radiolabeled authentic PIG(-P) structure as described in "Müller et al., Endocrinology 138, 3459-3475, 1997"; was used; YCN-PIG prepared from the radiochemically pure GPI protein, Gce1p, of the plasma membrane from *S. cerevisiae*, which had been metabolically labeled with myo-[$^{14}C$]inositol, by sequential proteolytic and lipolytic cleavages in vitro. For assessing the structure-activity relationship for binding, chemically synthesized YCN-PIG and derivatives thereof were used. (FIG. 1: YCN-PIG; FIG. 2: YMN-PIG; FIG. 3: PIG37; FIG. 4: YCN)

Synthesis of the tripeptide of YCN-PIG was performed by means of state of the art peptide synthesis. The hexasaccharide was synthesized using the trichloroacetimide method as described in "Frick et al., Biochemistry 37, 13421-13436; 1998". The critical step in synthesis of PIG-P turned out to be the formation of the phosphodiester bond. Among various procedures tested the H-phosphonate method produced the most yield.

Deprotection of the final compounds was performed under sodium in liquid $NH_3$ enforced by the presence of cysteine (no hydration possible with palladium) and acid-labile cyclic phosphate. All compounds were characterized by mass, $^1$H-NMR, $^{13}$C-NMR and $^{31}$P-NMR spectroscopy.

PIG(-P) Specifically Bind to hcDIGs

Total plasma membranes prepared from unstimulated adipocytes by differential centrifugation were enriched (vs. total cell lysates) for specific marker enzymes of the plasma membrane. Quabain-sensitive p-nitrophenylphosphatase (corresponding to the catalytic subunit of the $Na^+/K^+$-ATPase) was enriched 9.5-fold and Nuc 10.9-fold (according to enzymic activities), $\beta_1$-integrin 13.9-fold and syntaxin-1 16.4-fold (according to immunoblotting) and Gce1 7.8-fold (according to photoaffinity labelling). Simultaneously, the plasma membrane preparation was deprived (vs. total cell lysates) of the sarcoplasmic reticulum marker, EGTA-sensitive $Ca^{2+}$-adenosine triphosphatase 5.7-fold and of the endosomal markers, SCAMP (Secretary Carrier Membrane Protein) 37/39 8.5-fold and GLUT4 (Glucose Transporter 4) 16.9-fold (according to immunoblotting). Microsomes from unstimulated adipocytes were enriched vs. total cell lysate for GLUT4 by 14.4-fold, SCAMP 37/39 by 8.5-fold, transferrin receptor by 6.9-fold and IGFII receptor by 9.7-fold and deprived vs. total cell lysates of p-nitrophenyl-phosphatase by 24.6-fold, Gce1 by 12.5-fold, Nuc by 15.8-fold, $\beta_1$-integrin by 39.5-fold and syntaxin-1 by 48.5-fold according to immunoblotting and of $Ca^{2+}$-sensitive adenosine triphosphatase activity by 19.9-fold. This indicates that this fraction represented primarily endoplasmic reticulum and endosomal structures and was virtually devoid of plasma membranes and sarcoplasmic reticulum fragments. hsDIGs and lcDIGs were prepared from unstimulated adipocytes on basis of their insolubility in 0.5 M $Na_2CO_3$ (pH 11) and low buoyant density in sucrose density gradient centrifugation. They were characterized by their deprivation (vs. total plasma membranes) of GLUT4 and the insulin receptor $\beta$-subunit. hcDIGs and lcDIGs differed from one another in significantly higher enrichment of caveolin, pp59$^{Lyn}$ and Gce1 in hcDIGs compared to lcDIGs.

Isolated subcellular membrane fractions were incubated with increasing amounts of radiolabeled YCN-PIG and the incubation terminated by rapid separation from the incubation medium by centrifugation through an oil layer of appropriate density.

Figure 5:
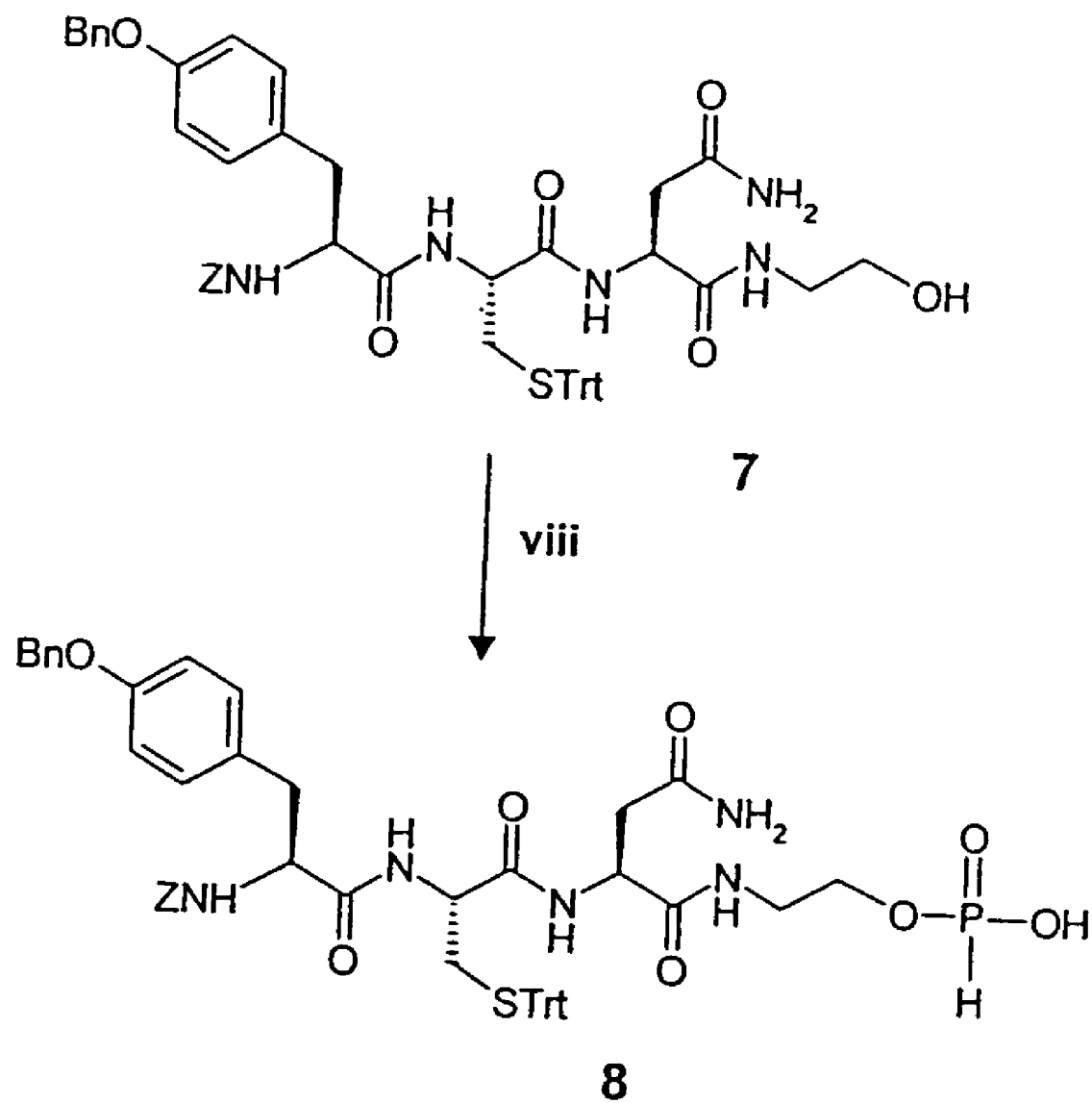
FIG. 5: Synthesis of YCN-PIG, part 2.

Membrane-associated YCN-PIG was recovered predominantly with hcDIGs in concentration-pependent and saturable fashion and to a minor degree with lcDIGs, whereas plasma membranes and microsomes were virtually devoid of radiolabel (FIG. 5). Within the linear range, unspecific binding of YCN-PIG to hcDIGs accounted for less than 20% as assessed by the presence of a 500 fold excess of unlabeled synthetic YCN-PIG or other competitors (FIG. 5). The following experiments were performed using a concentration of YCN-PIG, corresponding to the end of the linear range of binding.

Figure 6:
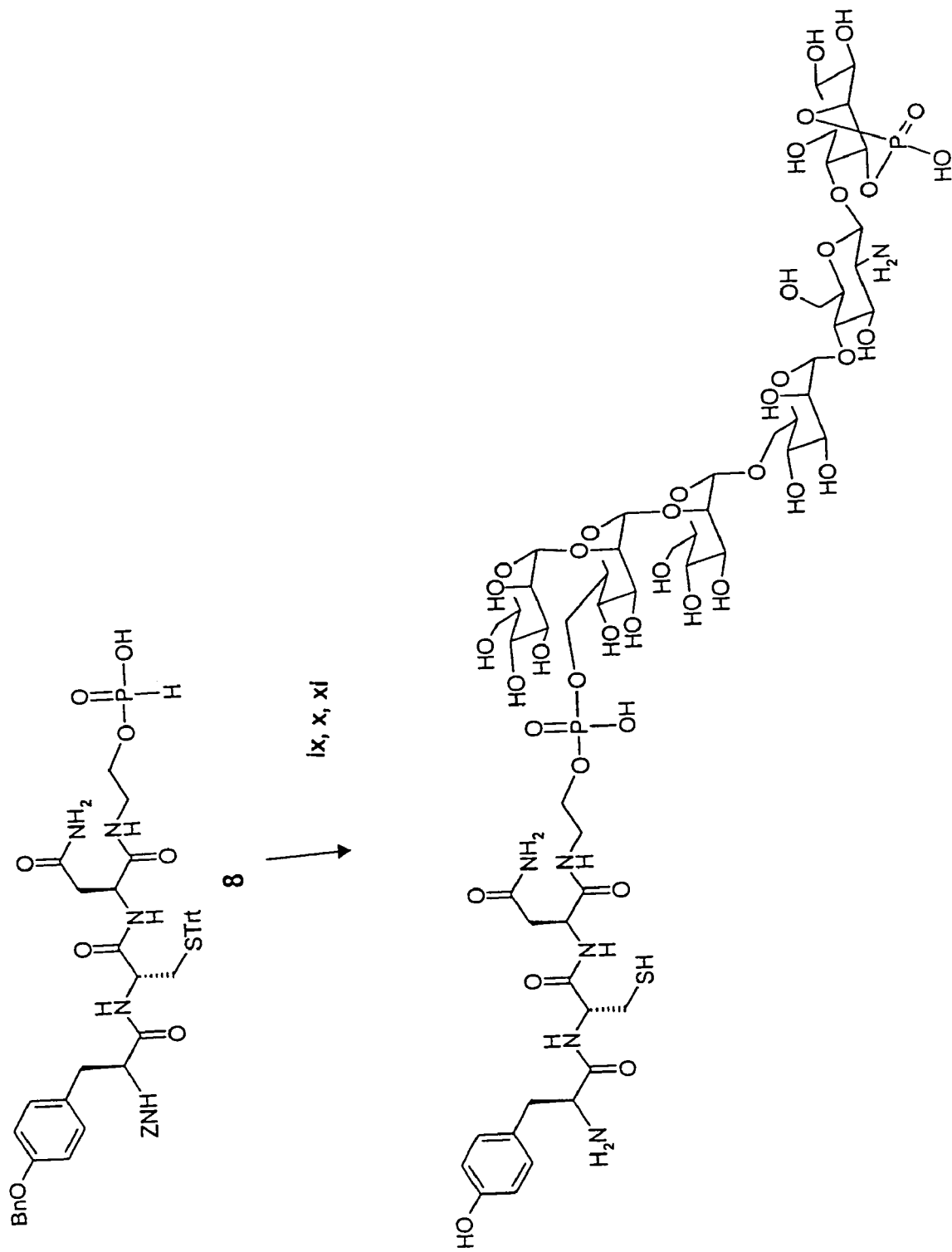
FIG. 6: Synthesis of YCN-PIG, part 3.

Other methods for determination of receptor-ligand interaction, such as rapid filtration and centrifugation on basis of sedimentation rather than density, failed to detect specific binding of YCN-PIG to any adipocyte membrane subfraction (data not shown), presumably due to the medium binding affinity and/or high dissociation rate. Scatchard plot analysis for YCN-PIG revealed a $K_d$ in the range of 50 nM-500 nM and a $B_{max}$ of 50-200 pmol per mg protein of hcDIGs. The specificity of binding of YCN-PIG to hcDIGs was demonstrated by significantly reduced efficacy of the peptide variants, YMN-PIG and PIG37 lacking the peptidylethanolamidyl moiety, as well as the very low activity of the peptidylethanolamidyl moiety, YCN, alone in the competition assay (FIG. 6).

A combination of unlabeled YCN plus PIG37 (equimolar ratio) displaced binding of radiolabeled YCN-PIG to hcDIGs only slightly less efficiently than unlabeled YCN-PIG and more potently than either the PIG or peptidylethanolamidyl moiety alone as well as YMN-PIG. This finding demonstrates simultaneous and synergistic recognition of the PIG and peptidylethanolamidyl moieties. The $IC_{50}$ for competition was just 3 to 4 fold higher for YCN plus PIG37 compared to covalently linked YCN-PIG (FIG. 6). Further it was studied whether the identified binding site for PIG(-P) is of proteinaceous nature. hcDIGs were pretreated with trypsin/NaCl or NEM and then incubated with increasing concentrations of radiolabeled YCN-PIG in the absence or presence of excess of unlabeled synthetic YCN-PIG (for evaluation of unspecific binding).

Figure 7:
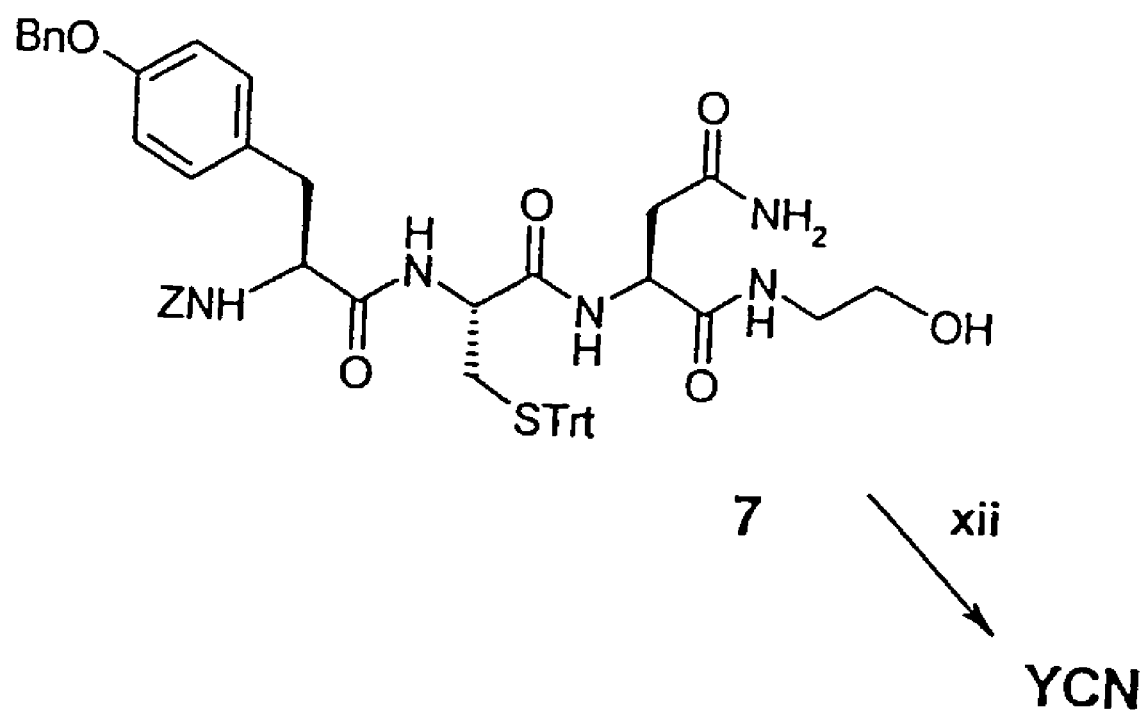
FIG. 7: Synthesis of YCN.
Figure 8:
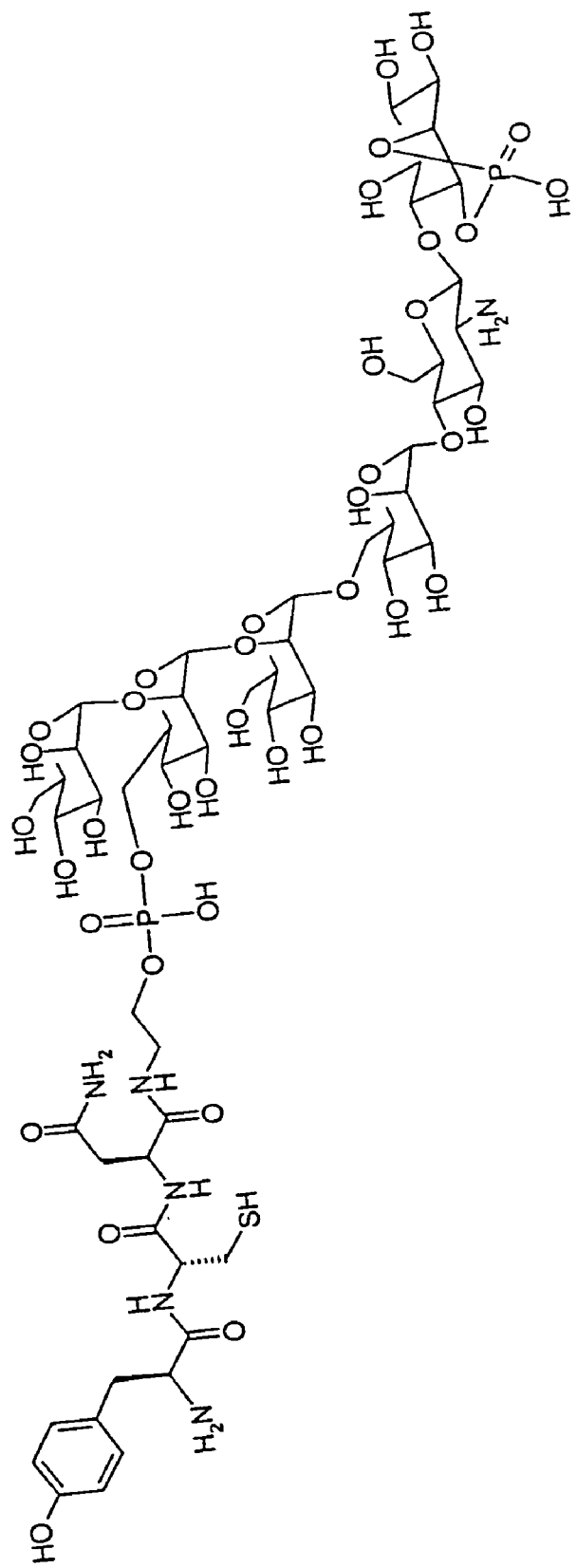
FIG. 8: Chemical formula of YCN-PIG.

Sequential treatment with trypsin and 0.5 M NaCl or treatment with NEM completely abrogated specific binding of radiolabeled YCN-PIG to hcDIGs, whereas trypsin or NaCl alone or NEM in the presence of DTT had no significant effect (FIG. 7). The identical inactivation pattern was observed for the lower affinity interaction of YCN-PIG with lcDIGs. These data demonstrate the existence of a trypsin/NaCl and NEM-sensitive binding protein for PIG(-P) at DIGs of the adipocyte cell surface. The preference of YCN-PIG for binding to hcDIGs compared to lcDIGs was confirmed by their conversion in course of cholesterol depletion of the adipocytes plasma membrane using m-$\beta$CD and subsequent analysis of hc/lcDIGs for specific binding of radiolabeled YCN-PIG. In control adipocytes, the major portion of YCN-PIG was recovered along with hcDIGs compared to 20% left associated with lcDIGs (FIG. 8). However, treatment of intact rat adipocytes with m-$\beta$CD (1-10 mM) revealed a concentration-dependent decline in the amount of YCN-PIG bound to hcDIGs accompanied by corresponding increase at lcDIGs. Trypsin/NaCl or NEM treatment of the adipocytes after cholesterol depletion but before preparation of the DIGs significantly impaired specific binding of YCN-PIG to both hcDIGs and lcDIGs (data not shown). These findings demonstrate the predominant location of the PIG(-P) receptor in hcDIGs of rat adipocytes the formation of which critically depends on cholesterol.

A Lipolytically Cleaved GPI Protein Specifically Binds to hcDIGs

The PIG moiety, —NH—$(CH_2)_2$O—PO(OH)O-6Man$\alpha$1 (Man$\alpha$1-2)-2Man$\alpha$1-6Man$\alpha$1-4GluN1-6Ino-1,2-(cyclic)-phosphate, of YCN-PIG, YMN-PIG and PIG37 (FIGS. 1, 2 and 3) is identical to the polar core glycan head group of all eucaryotic GPI proteins. Consequently, it was studied whether the proteinaceous binding site for PIG-P interacts with lcGPI proteins, i.e. whether it recognizes the PIG(-P) moiety if attached to the complete polypeptide portion of a GPI protein. In order to obtain a radiolabeled lcGPI protein, Gce1p from metabolically labeled S. cerevisiae cells was treated with PI-specific PLC (B. cereus) and the hydrophilic cleavage product purified to radiochemical homogeneity.

Figure 9:
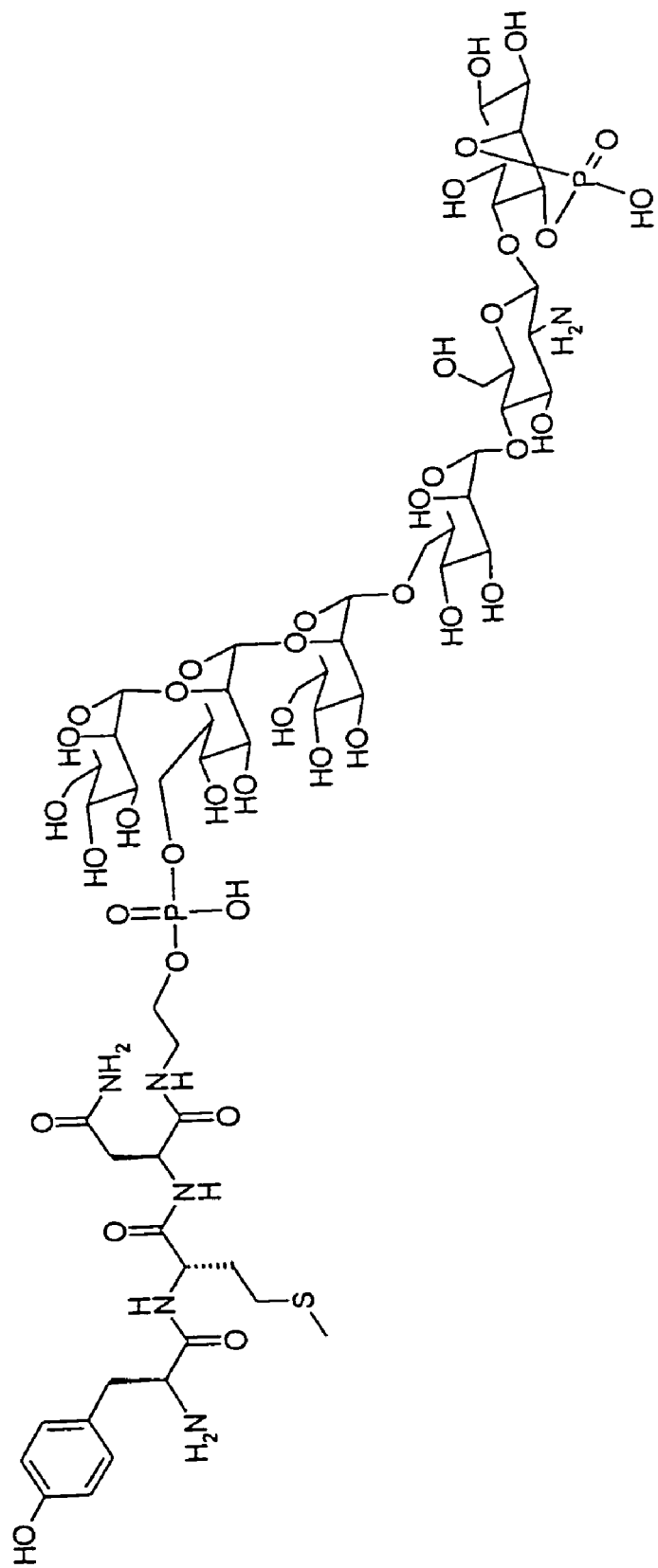
FIG. 9: Chemical formula of YMN-PIG.

Using the same oil-centrifugation-method as for PIG(-P), it was found that IcGce1p associated with DIGs from isolated rat adipocytes in a concentration-dependent and saturable fashion with hcDIGs being 11- to 15-fold more efficient than lcDIGs. Unspecific binding in the presence of a 200 fold molar excess of unlabeled IcGce1p accounted for less than 15% of the total IcGce1p recovered with DIGs at non-saturating concentrations of IcGce1p. According to Scatchard plot analysis, the $K_d$ for IcGce1p binding to hcDIGs is in the range of 0.1-1 μM with $B_{max}$ of 70-200 pmol per mg protein of hcDIGs. Total plasma membranes and microsomes did not exhibit specific binding of IcGce1p. Thus, hcDIGs of the adipocyte plasma membranes apparently harbor specific binding sites for IcGce1p from yeast. For further analysis of the identity of the binding sites for PIG(-P) and IcGPI proteins as indicated by the similar $K_d$ and $B_{max}$ values, the relative affinities of the synthetic PIG(-P) compounds for the IcGce1p binding site at hcDIGs were compared in competition studies (FIG. 9).

Figure 10:
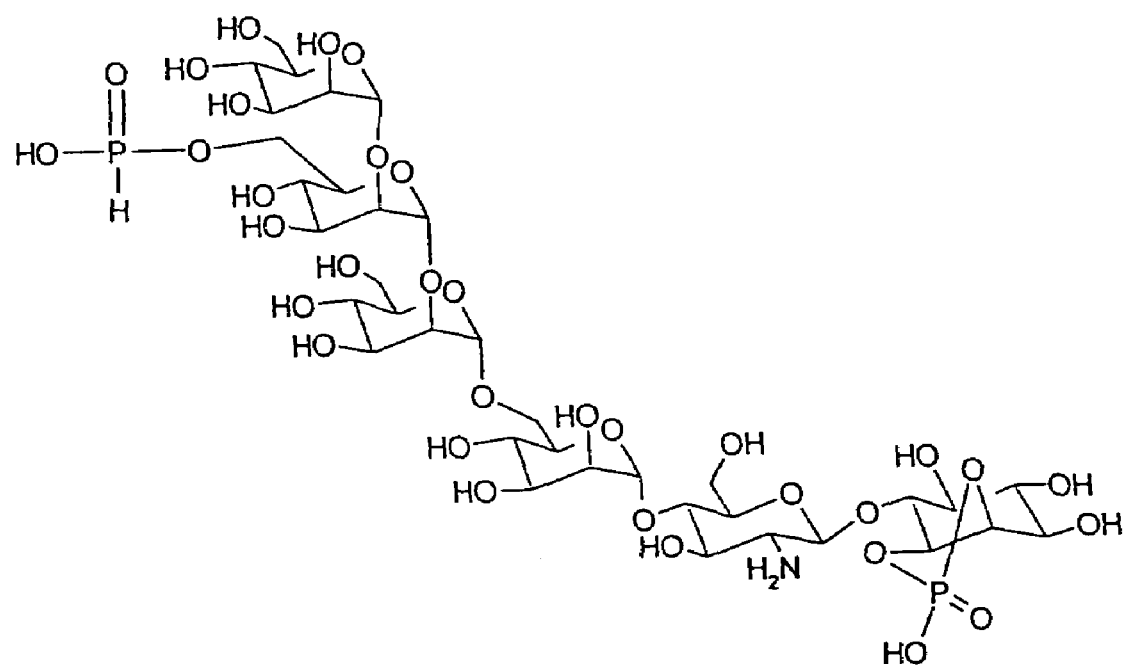
FIG. 10: Chemical formula of PIG37.

The binding of radiolabeled IcGce1p to hcDIGs was displaced by excess (more than 500 fold) of labeled synthetic YCN–PIG, YMN-PIG and YCN plus PIG37 by more than 75% of total IcGce1p bound confirming the specificity of the interaction of IcGce1p with hcDIGs. Competition of IcGce1p binding with PIG37 and YCN was considerably less efficient. The relative ranking of the different PIG(-P) as reflected in their apparent $IC_{50}$ for displacing IcGce1p from hcDIGs was YCN–PIG>YCN+PIG37>YMN-PIG>PIG37>YCN and is, thus, identical to that for interference with YCN–PIG binding (FIG. 6). Moreover, the apparent $IC_{50}$ values were very similar for competition of IcGce1p and YCN–PIG binding arguing that in both cases the same determinants are recognized and the residual protein moiety of the GPI protein (except of the carboxy-terminal tripeptidylethanolamidyl residue) does not contribute to binding. Next the sensitivity of the interaction of IcGce1p with hcDIGs toward trypsin/NaCl— and NEM-treatment of intact rat adipocytes was studied under conditions which almost completely disrupted binding of radiolabeled YCN–PIG (FIG. 7). hcDIGs from trypsin/NaCl— as well as NEM-treated adipocytes displayed association of radiolabeled IcGce1p not exceeding unspecific binding in the presence of a 500 fold excess of unlabeled YCN–PIG (which accounts for about 30% of total Gce1p recovered with hcDIGs from untreated control cells) (FIG. 10). In contrast, incubation of the adipocytes with NEM in the presence of excess of DTT (FIG. 10) or with either trypsin or NaCl alone (data not shown) did not impair binding of radiolabeled IcGce1p and its competition by 3 μM YCN+PIG37, 5 μM PIG37 and 10 μM YCN compared to untreated cells. Taken together, the specific binding sites for YCN–PIG and IcGce1p display very similar characteristics with regard to localization at hcDIGs of the adipocyte plasma membrane, absolute and relative affinities (to structural derivatives), expression level and sensitivity toward both trypsin/NaCl and NEM.

Endogenous Ligands for the Receptor for PIG(-P) and IcGPI Proteins

Candidates for physiological ligands of the apparently identical binding sites for PIG(-P) and IcGPI proteins are uncleaved GPI structures, i.e. GPI lipids and/or GPI protein anchors. To test this possibility, isolated rat adipocytes were subjected to treatment with various GPI-specific PLs and subsequent salt wash (0.5 M NaCl) prior to preparation of hcDIGs in order to specifically remove putative endogenous GPI molecules which interact with the receptor and thereby mask the binding sites for YCN–PIG/IcGce1p.

Figure 11:
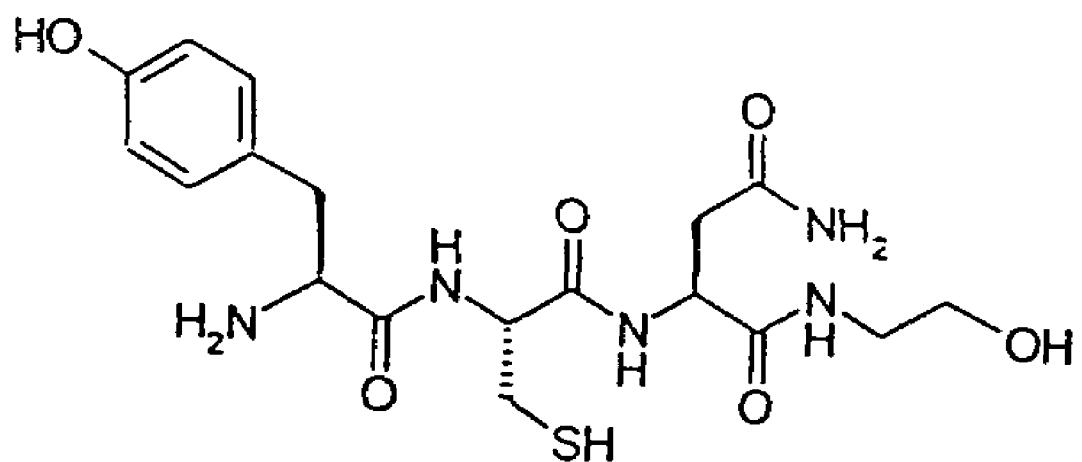
FIG. 11: Chemical formula of YCN.

Incubation of rat adipocytes with increasing concentrations of PI-specific PLC from *B. cereus* or GPI-specific PLD from human serum resulted in a concentration-dependent increase in the amounts of radiolabeled YCN–PIG and Gce1p which specifically bind to hcDIGs (FIG. 11). The efficiency of the lipolytic digestions was demonstrated in parallel by the loss of Gce1p and Nuc from hcDIGs.

Figure 12:
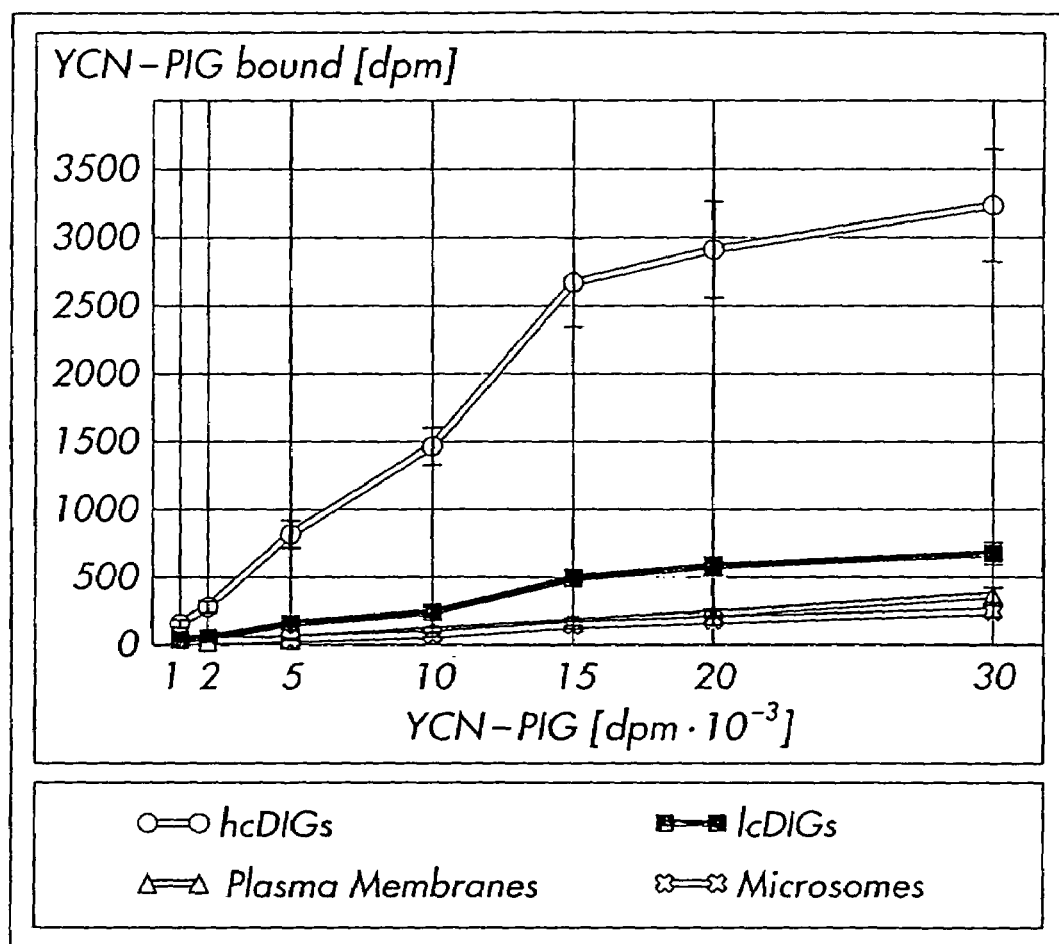
FIG. 12: Specific binding of PIG(-P) to hcDIGs.

Their losses by 75 and 65%, respectively, correlated with the increase in binding of YCN–PIG or IcGce1p to hcDIGs by 200 and 260%. The specificity of the GPI cleavages was demonstrated by the complete failure of PC-specific PLC (*B. cereus*) and PLD from cabbage (which do not attack GPI structures) to significantly displace Gce1 or Nuc from hcDIGs as well as to stimulate YCN–PIG (IcGce1p) binding to hcDIGs (FIGS. 11, 12). Scatchard plot analysis of specific binding to hcDIGs from PI-specific PLC-prepreated adipocytes (unspecific binding was not significantly altered) revealed that the increased association of radiolabeled YCN–PIG/IcGce1p was mainly due to the 2 to 3 fold higher $B_{max}$ with almost unaltered $K_d$. These findings demonstrate that about 50% of the binding sites for PIG(-P) or IcGPI proteins at hcDIGs in isolated rat adipocytes in the basal state are occupied by endogenous GPI structures cleavable by (G)PI-specific PLC/D. Remarkably, insulin at a physiological concentration mimicked the effect of GPI-specific PLC/D treatment in rat adipocytes to a certain degree causing a moderate, but significant, decline in the amounts of Gce1p and Nuc in hcDIGs. Insulin-induced loss of GPI proteins from hcDIGs led to marked increase of binding capacities for YCN–PIG or IcGce1p (FIGS. 11, 12).

Furthermore, it could be demonstrated that the receptor for PIG(-P) and IcGPI proteins is identical to the trypsin/NaCl and NEM-sensitive 115 kDa protein which was called CIR.

Binding of PIG-P to the receptor will affect its accessibility to subsequent covalent modification by NEM and/or cleavage and release from the adipocyte cell surface by trypsin/NaCl.

Figure 13:
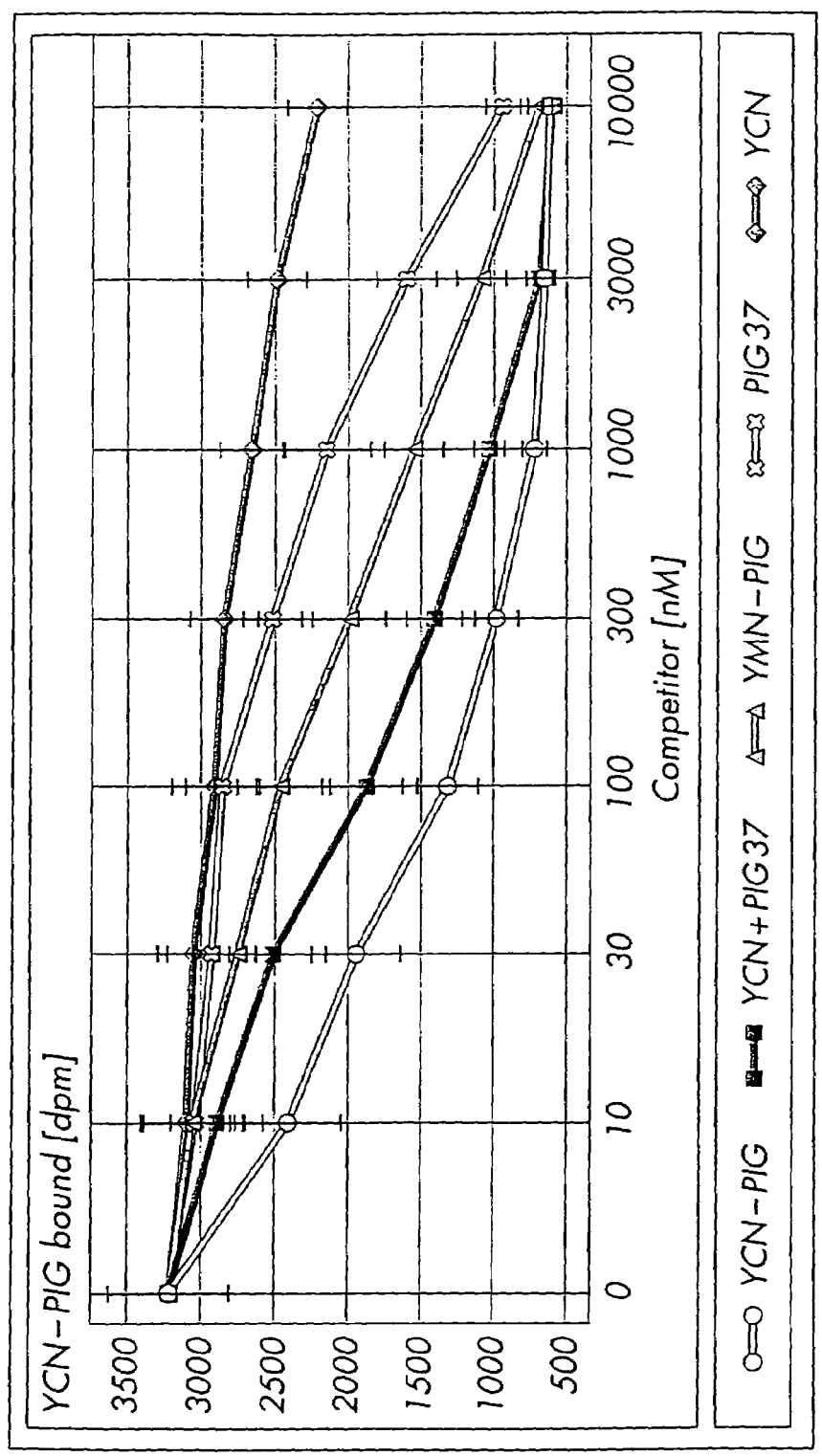
FIG. 13: Specific binding of PIG-P to hcDIGs.

Rat adipocytes were incubated with PIG(-P) and then sequentially subjected to labeling with [$^{14}$C]NEM and treatment with trypsin/NaCl. Analysis of the released radiolabeled polypeptides by SDS-PAGE and phosphorimaging revealed (FIG. 13) that PIG(-P) reduced crosslinking of a 115 kDa polypeptide by [$^{14}$C]NEM and/or its recovery from the infranatant of adipocytes after trypsin/NaCl-treatment. The reduction by YCN–PIG or PIG37 at 3 μM and YCN at 30 μM was 83, 65 and 28%, respectively, compared to control cells. This protein represented the only major NEM-labeled component which was released from plasma membranes by trypsin/NaCl but not by either treatment alone (FIG. 13) and is identical with CIR. In agreement with experimental evidence for the existence of endogenous ligands (e.g. GPI proteins) and their removal from the corresponding binding site by lipolytic cleavage (see FIGS. 11, 12), treatment of adipocytes with exogenous PI-specific PLC (*B. cereus*) or insulin slightly but reproducibly stimulated the trypsin/NaCl-dependent release of [$^{14}$C]NEM-labeled CIR by 30 and 20%, respectively (FIG. 13). Since the relative ratio of release of CIR from the adipocyte cell surface by trypsin/NaCl-vs. trypsin-vs. NaCl-treatment (100/20/10) was roughly comparable in control, PIG(-P)-stimulated and PLC/insulin-treated cells, binding of PIG (-P) and endogenous GPI ligands to hcDIGs apparently impairs labeling of CIR by NEM rather than its tryptic cleavage. This is caused by a conformational change in CIR elicited by the interaction of ligands with the PIG(-P) receptor at hcDIGs of the adipocyte plasma membrane.

TABLE 1

$^1$H and $^{13}$C chemical shifts [ppm] for YCN-PIG in $D_2O$, pD = 8.1 (uncorr.)

| Residue | Position | $^1$H [ppm] | $^{13}$C [ppm] |
|---|---|---|---|
| Tyrosine | CO | — | ? |
| | α | 4.12 | 55.18 |
| | β | 2.99, 3.03 | 37.05 |
| | γ | — | 125.90 |
| | δ | 7.05 | 131.20 |
| | ε | 6.77 | 116.57 |
| | ζ | — | 155.30 |
| Cysteine | CO | — | ? |
| | α | 4.56 | n.d. |
| | β | 2.64, 2.71 | 37.35 |
| Asparagine | CO | — | n.d. |
| | α | 4.58 | n.d. |
| | β | 2.89, 3.05 | 37.05 |
| | γ-CO | — | ? |
| Ethanolamine | 1 | n.d. | n.d. |
| | 2 | n.d. | n.d. |
| Mannose 1 | 1 | 4.93 | 102.84 |
| | 2 | 3.96 | 70.83 |
| | 3 | 3.73 | 71.05 |
| | 4 | 3.64 | 67.19 |
| | 5 | 3.67 | 73.91 |
| | 6 | n.d. | n.d. |
| Mannose II | 1 | 5.18 | 101.40 |
| | 2 | 4.01 | 79.10 |
| | 3 | 3.87 | 70.60 |
| | 4 | 3.70 | 67.12 |
| | 5 | 3.76 | 72.87 |
| | 6 | n.d. | n.d. |
| Mannose III | 1 | 4.98 | 99.07 |
| | 2 | 3.89 | 79.69 |
| | 3 | 3.59 | 73.45 |
| | 4 | n.d. | n.d. |
| | 5 | n.d. | 70.85 |
| | 6 | n.d. | n.d. |
| Mannose IV | 1 | 5.08 | 102.62 |
| | 2 | 3.95 | 70.91 |
| | 3 | 3.68 | 71.08 |
| | 4 | 3.51 | 67.60 |
| | 5 | 3.73 | 73.21 |
| | 6 | n.d. | 67.15 |
| Glucosamine | 1 | 4.86 | 100.12 |
| | 2 | 3.00 | 57.00 |
| | 3 | 3.75 | 72.89 |
| | 4 | 3.58 | 77.88 |
| | 5 | 3.46 | 75.99 |
| | 6 | 3.65, 3.78 | 61.68 |
| Inositol | 1 | 4.35 | 78.52 |
| | 2 | 4.62 | 78.09 |
| | 3 | 3.62 | 70.24 |
| | 4 | 3.56 | 72.60 |
| | 5 | 3.37 | 72.57 |
| | 6 | 3.96 | 82.39 |

Specific binding of PIG(-P) to hcDIGs is shown in FIG. 12.

Increasing amounts of radiolabeled YCN–PIG isolated from S. cerevisiae were incubated (1 h, 4° C.) with hcDIGs (6.5 μg protein), lcDIGs (6.5 μg), plasma membranes (47.5 μg) and microsomes (68 μg) from isolated rat adipocytes. The membrane fractions/DIGs were subjected to oil-layer-centrifugation, recovered with/from the pellet/top of the oil layer, solubilized and counted for radioactivity. Specific binding was calculated as the difference between radioactivity measured in the absence and presence of 10 μM unlabeled YCN–PIG. Each point represents the mean±SD of triplicate incubations using at least 4 different membrane preparations.

Specific Binding of PIG-P to hcDIGs is Shown in FIG. 13

Radiolabeled YCN–PIG (18,000-22,000 dpm) was incubated (1 h, 4° C.) with hcDIGs (6.5 μg protein) in the absence or presence of increasing amounts of unlabeled YCN-PIG, YCN+PIG37, YMN-PIG, PIG37 and YCN (Competition). The membrane fractions/DIGs were subjected to oil-layer-centrifugation, recovered with/from the pellet/top of the oil layer, solubilized and counted for radioactivity.

Figure 14:
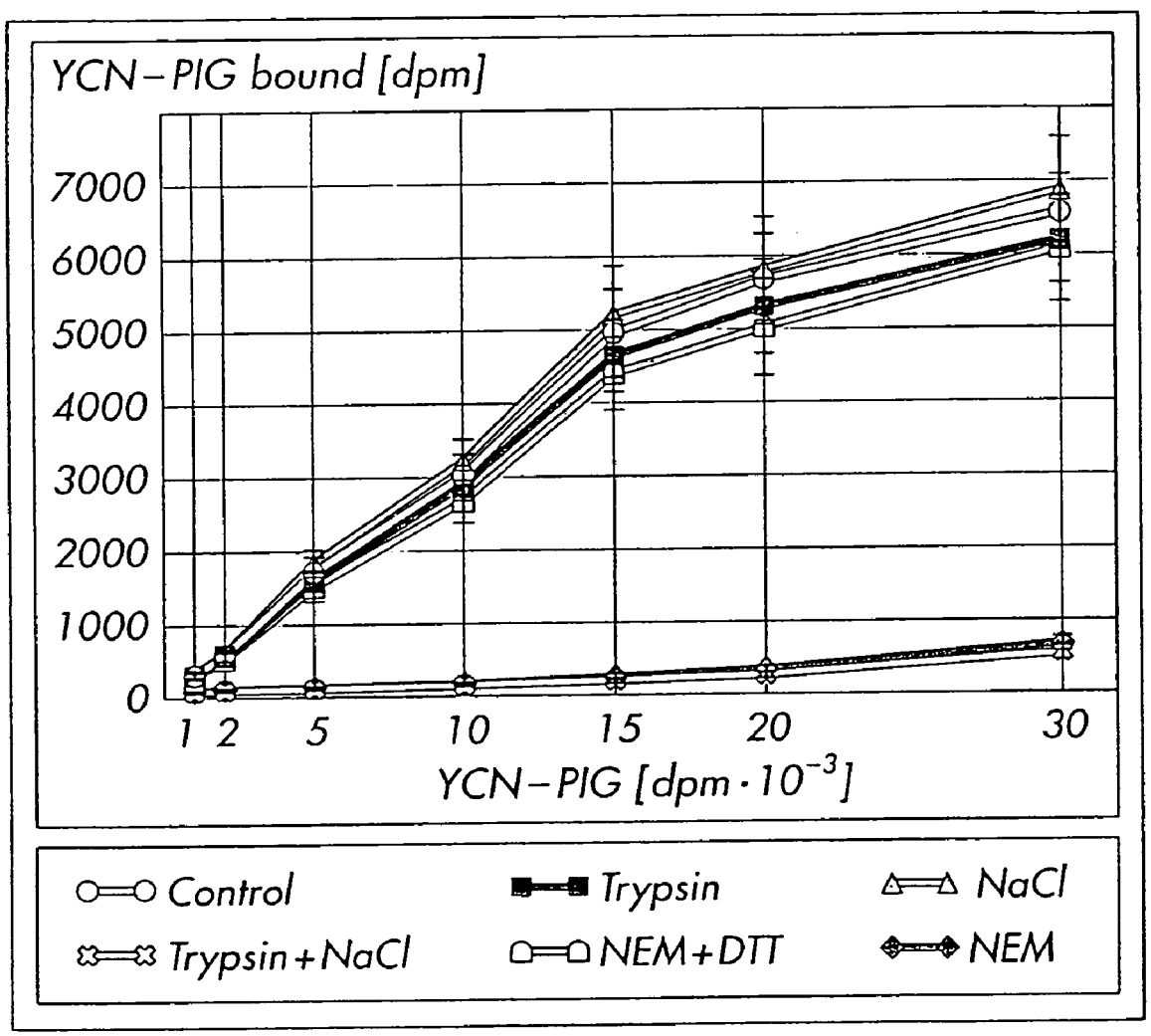
FIG. 14: Characterization of the binding site for PIG-P at hcDIGs.

Characterization of the Binding Site for PIG-P at hcDIGs is Shown in FIG. 14.

Increasing amounts of radiolabeled YCN-PIG isolated from S. cerevisiae were incubated (1 h, 4° C.) with hcDIGs (6.5 μg protein) from isolated rat adipocytes which had been pretreated with trypsin/NaCl, trypsin, NEM+DTT, NaCl or NEM or left untreated (Control). DIGs were subjected to oil-layer-centrifugation, recovered from top of the oil layer, solubilized and counted for radioactivity. Specific binding was calculated as the difference between radioactivity measured in the absence and presence of 10 μM unlabeled YCN-PIG. Each point represents the mean±SD of triplicate incubations using at least 3 different adipocyte pretreatments.

Figure 15:
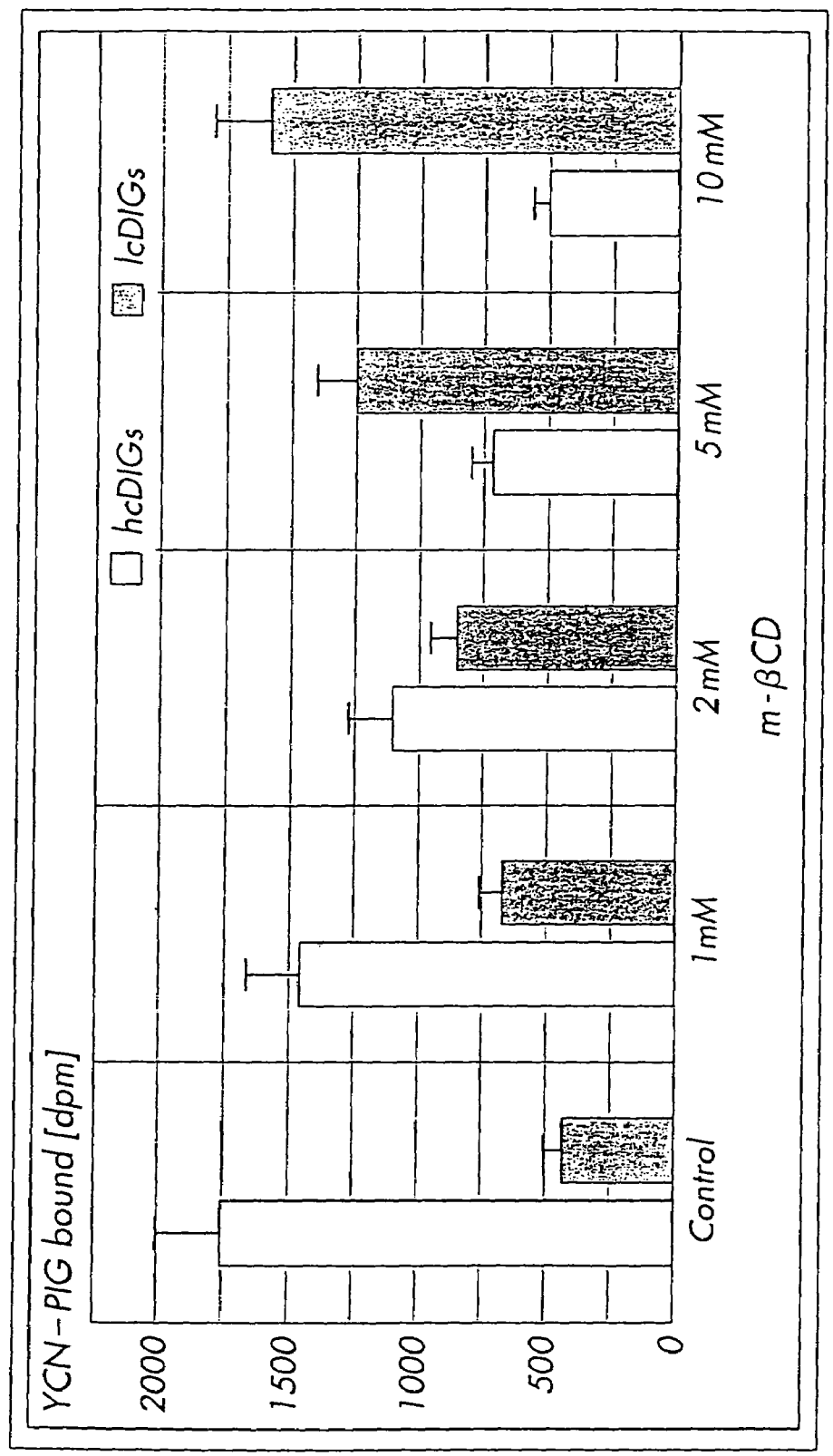
FIG. 15: Characterization of the binding site for PIG-P at hcDIGs.

Characterization of the Binding Site for PIG-P at hcDIGs is Shown in FIG. 15.

Radiolabeled YCN-PIG (12,000-18,000 dpm) was incubated (1 h, 4° C.) with the (proportional) amounts of hcDIGs and lcDIGs prepared from isolated rat adipocytes which had been pretreated (50 min, 30° C.) with increasing concentrations of m-βCD or left untreated. DIGs were subjected to oil-layer-centrifugation, recovered from top of the oil layer, solubilized and counted for radioactivity measured in the absence and presence of 10 μM unlabeled YCN-PIG. Each point represents the mean±SD of triplicate incubations using at least 3 different adipocyte pretreatments.

Figure 16:
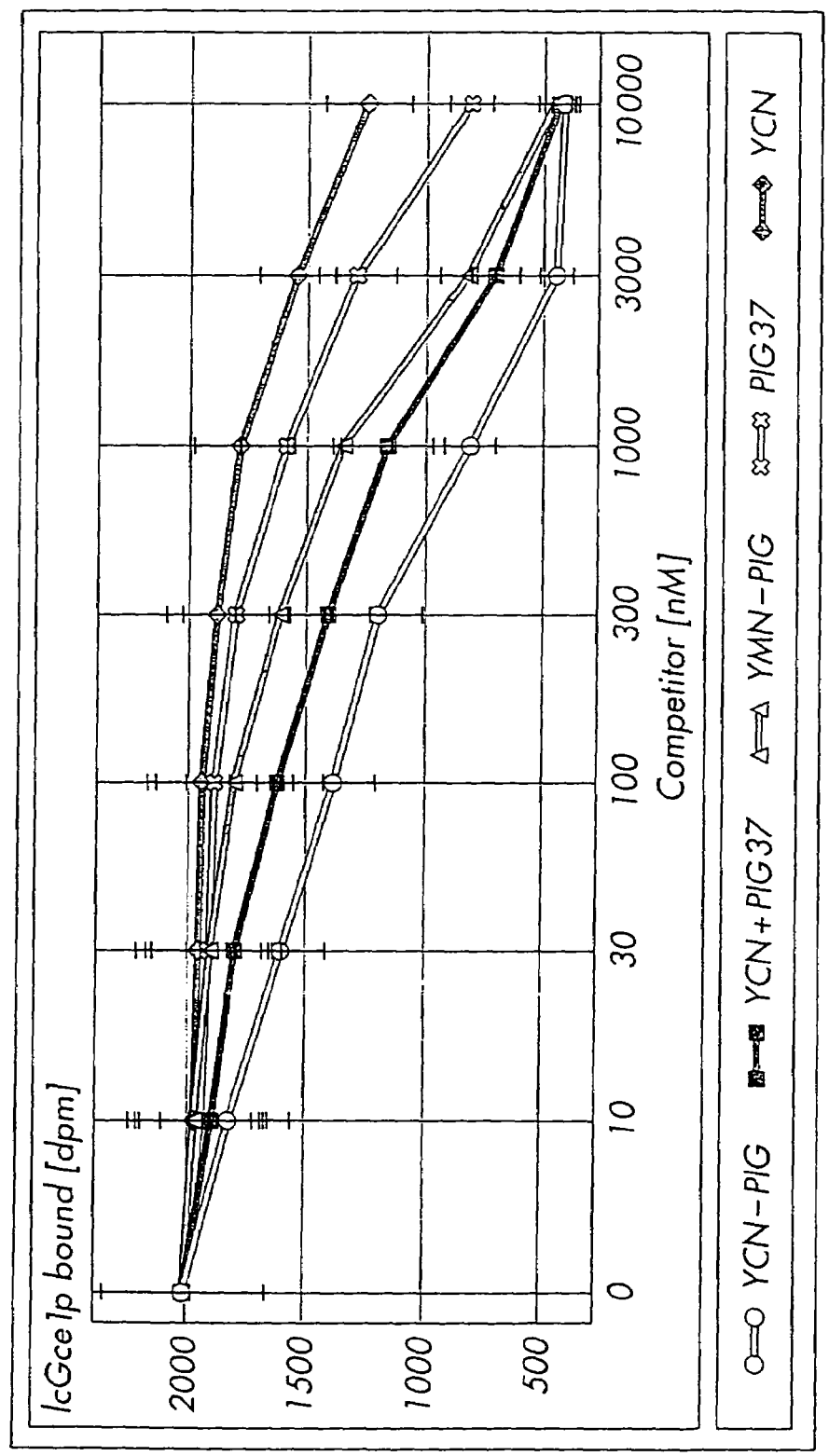
FIG. 16: Specific binding of IcGce1p to hcDIGs.

Specific Binding of lcGce1p to hcDIGs is Shown in FIG. 16.

Radiolabeled Gce1p prepared from S. cerevisiae and treated with PI-specific PLC (B. cereus) was incubated (1 h, 4° C.) with hcDIGs (6.5 μg protein) isolated from untreated rat adipocytes in the absence or presence of unlabeled PIG-P. hcDIGs were subjected to oil-layer-centrifugation, solubilized and counted for radioactivity. Each point represents the mean±SD of quadruplicate incubations using at least 3 different hcDIG preparations and adipocyte pretreatments, respectively.

Figure 17:
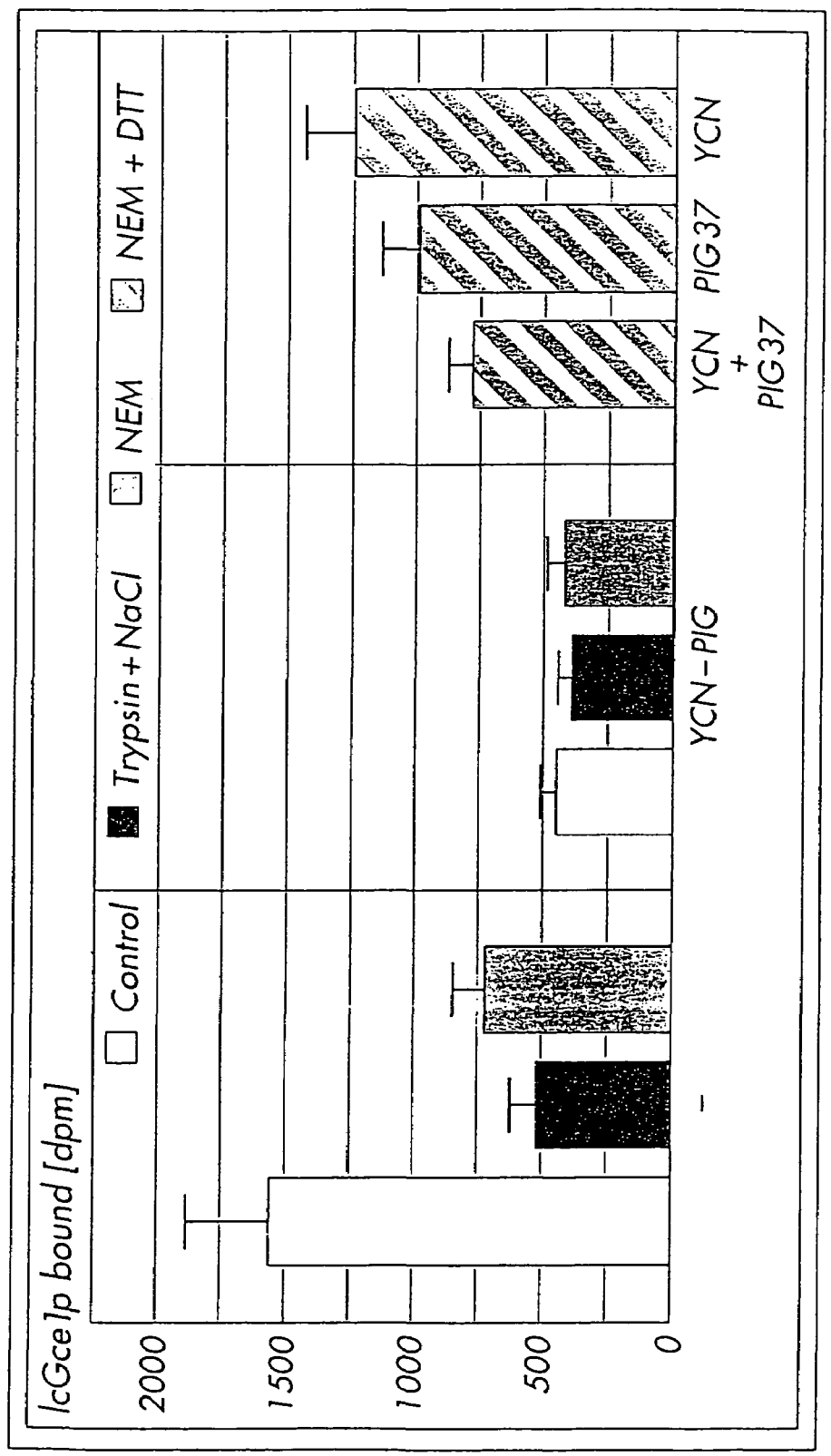
FIG. 17: Specific binding of IcGce1p to hcDIGs.

Specific Binding of lcGce1p to hcDIGs is Shown in FIG. 17.

Radiolabeled Gce1p prepared from S. cerevisiae and treated with PI-specific PLC (B. cereus) was incubated (1 h, 4° C.) with hcDIGs (6.5 μg protein) isolated from adipocytes which had been pretreated with trypsin/NaCl, NEM, NEM+DTT or left untreated (Control) in the absence or presence of unlabeled YCN-PIG (final conc. 3 μM), YCN+PIG37 (3 μM), PIG37 (5 μM) and YCN (10 μM). hcDIGs were subjected to oil-layer-centrifugation, solubilized and counted for radioactivity. Each point represents the mean±SD of quadruplicate incubations using at least 3 different hcDIG preparations and adipocyte pretreatments, respectively.

Figure 18:
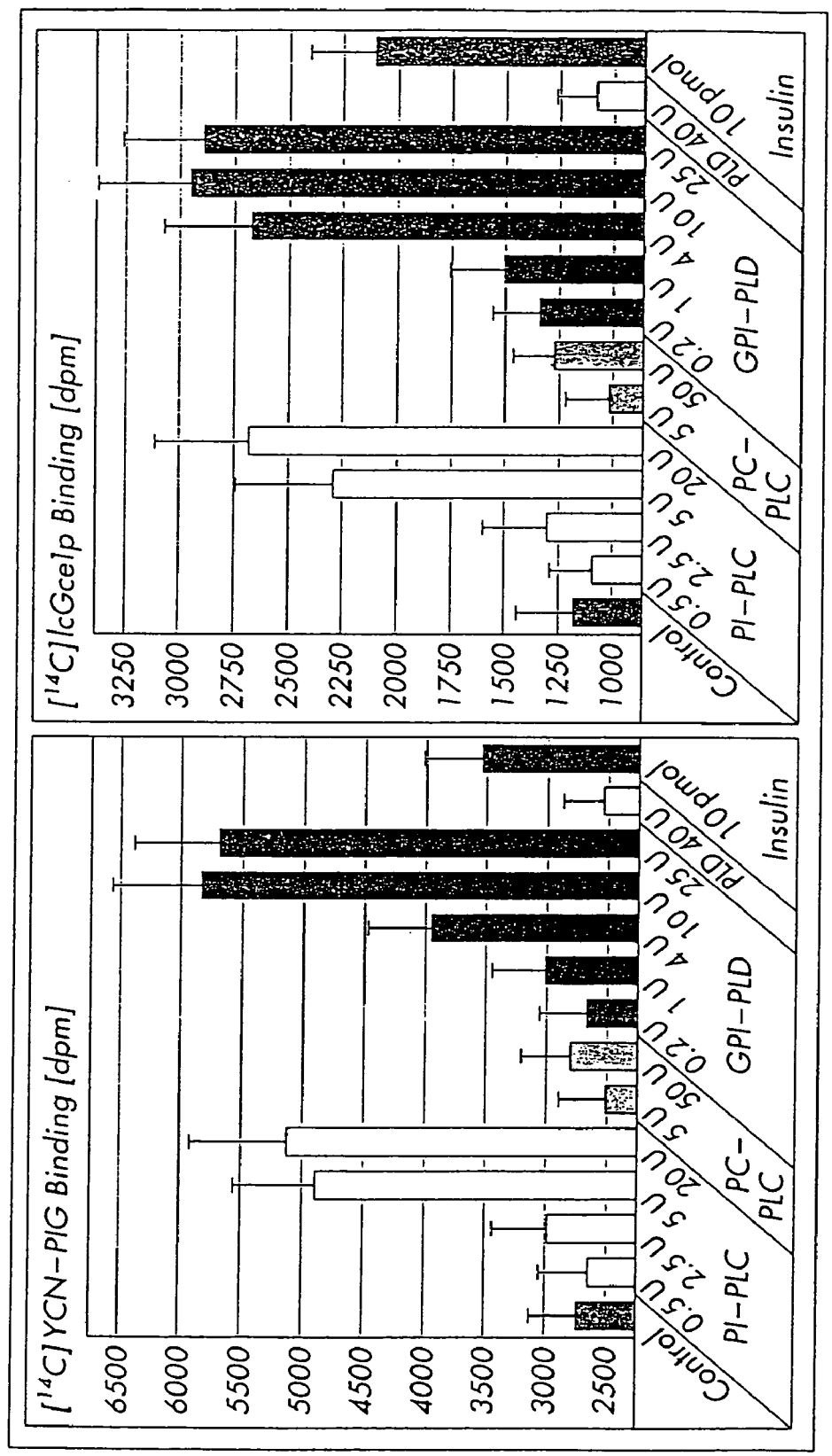
FIG. 18: Effect of PL and insulin treatment of adipocytes on binding of YCN-PIG and IcGce1p to hcDIGs.

Effect of PL and Insulin Treatment of Adipocytes on Binding of YCN-PIG and lcGce1p to hcDIGs is Shown in FIG. 18.

Isolated rat adipocytes (7×10$^7$ cells/ml) were incubated (30 min, 30° C.) with the indicated amounts of PI-specific PLC (B. cereus), PC-specific PLC (B. cereus), GPI-specific PLD (human serum) or PLD (cabbage) or human insulin in a total volume of 2 ml under mild shaking under 5% $CO_2$/95% $O_2$. After addition of 2 ml of 1 M NaCl, the adipocytes were washed by flotation. hcDIGs were isolated and 6.5 μg aliquots incubated (1 h, 4° C.) with radiolabeled lcGce1p prepared from S. cerevisiae and YCN-PIG (15,000-25,000 dpm) in the absence or presence of unlabeled YCN-PIG (final conc. 10 μM), subjected to oil-layer-centrifugation, recovered from top of the oil layer, solubilized and counted for radioactivity. Specific binding was calculated as the difference between absence and presence of YCN-PIG. Each point represents the mean±SD of triplicate incubations using at least two different hcDIGs preparations.

Figure 19:
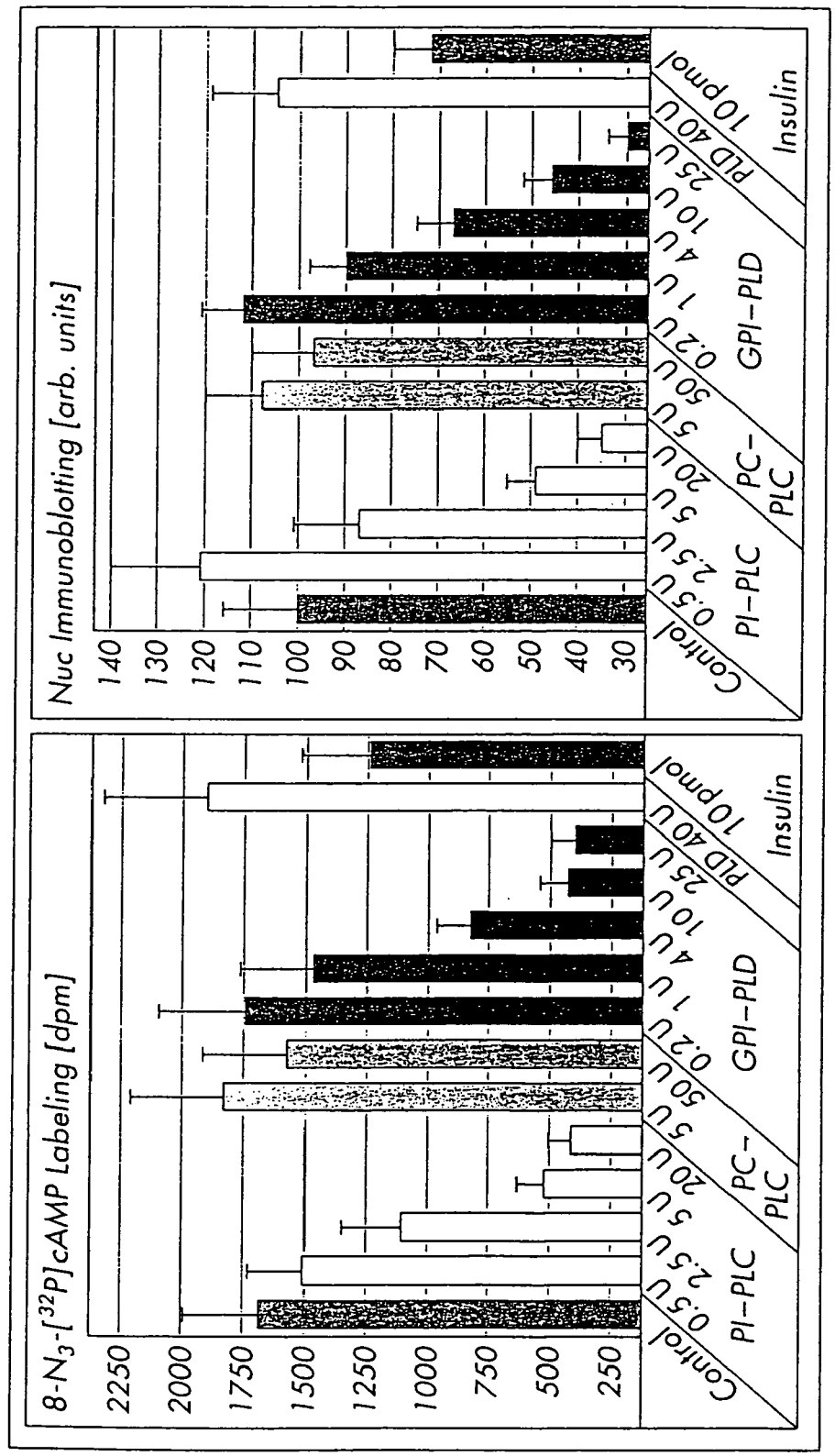
FIG. 19: Effect of PL and insulin treatment of adipocytes on binding of YCN-PIG and IcGce1p to hcDIGs.

Effect of PL and Insulin Treatment of Adipocytes on Binding of YCN-PIG and IcGce1p to hcDIGs is Shown in FIG. 19.

Isolated rat adipocytes ($7 \times 10^7$ cells/ml) were incubated (30 min, 30° C.) with the indicated amounts of PI-specific PLC (*B. cereus*), PC-specific PLC (*B. cereus*), GPI-specific PLD (human serum) or PLD (cabbage) or human insulin in a total volume of 2 ml under mild shaking under 5% $CO_2$/95% $O_2$. After addition of 2 ml of 1 M NaCl, the adipocytes were washed by flotation. hcDIGs were isolated and 6.5 µg aliquots incubated (1 h, 4° C.) with radiolabeled IcGce1p prepared from *S. cerevisiae* and YCN-PIG (15,000-25,000 dpm) in the absence or presence of unlabeled YCN-PIG (final conc. 10 µM), subjected to oil-layer-centrifugation, recovered from top of the oil layer, solubilized and counted for radioactivity.

Figure 20:
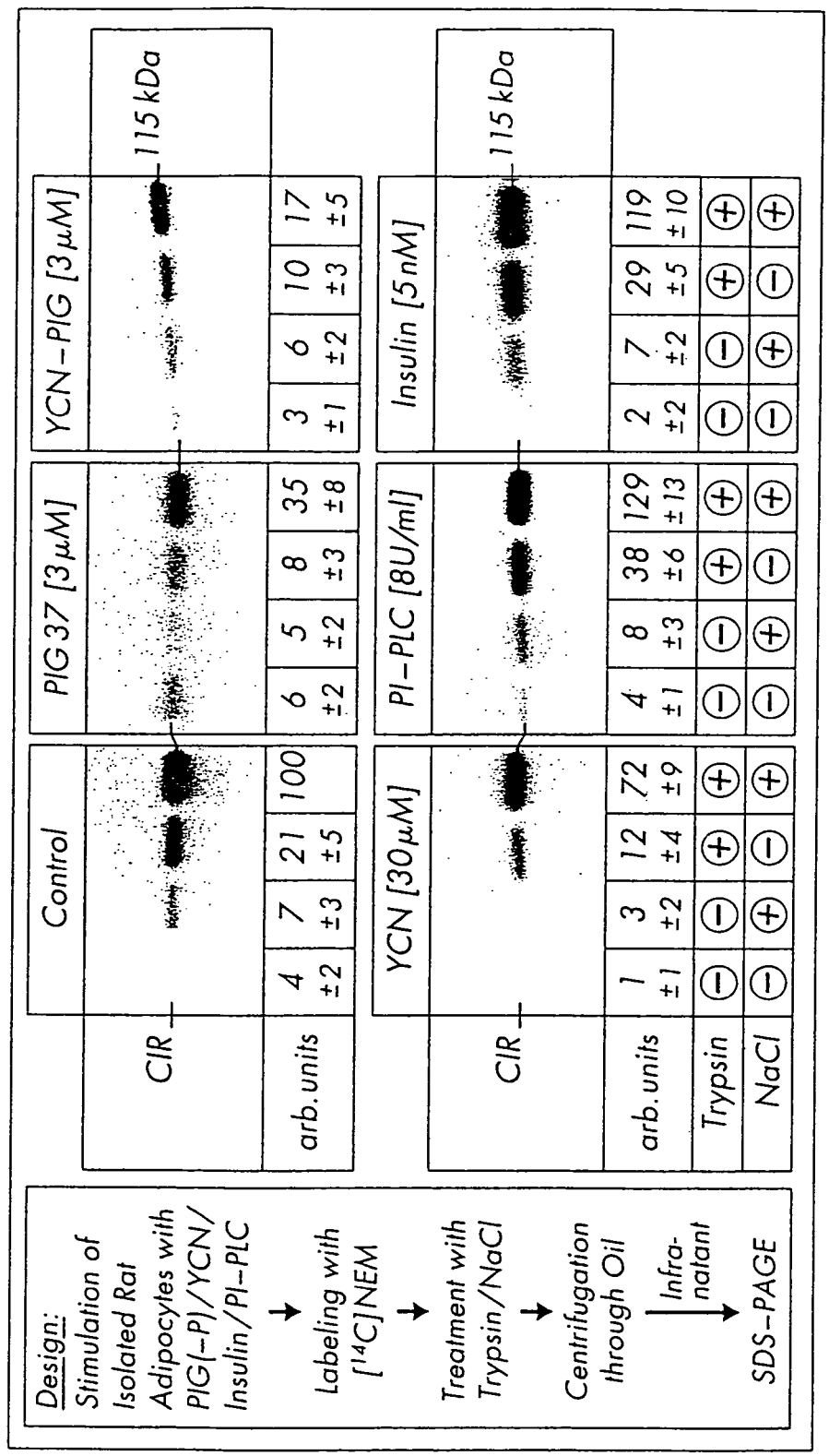
FIG. 20: Effect of PIG(-P), PI-specific PLC and insulin on NEM-labeling of CIR.

Effect of PIG(-P), PI-Specific PLC and Insulin on NEM-Labeling of CIR is Shown in FIG. 20.

Isolated rat adipocytes were incubated (30 min, 37° C.) in the absence (Control) or presence of PIG37, YCN-PIG, YCN, PI-PLC (*B. cereus*) or insulin at the concentrations given and then labeled with [$^{14}$C]NEM. After treatment with trypsin/NaCl as indicated, the adipocytes were separated from the incubation medium by centrifugation through an oil layer. Proteins were recovered from the medium (below the oil layer) and resolved by SDS-PAGE.

Phosphorimages are shown from a typical experiment repeated three times with similar results. Quantitative evaluation of four different adipocyte incubations with triplicate measurements given as arbitrary units (mean±SD) with the amount of CIR released from trypsin/NaCl-treated control cells set at 100.

All documents referred to herein are incorporated herein by reference in their entirety, including the priority document, EP 02015047.0, filed Jul. 5, 2002.

What is claimed is:

1. An isolated protein from the plasma membrane of an adipocyte, which has specific binding affinity to phosphoinositolglycan or a phosphoinositolglycan-peptide characterized by
   a) ability to trigger tyr phosphorylation of insulin receptor substrate 1 or 2 in an adipocyte after specific binding of a phosphoinositolglycan or a phosphoinositolglycan-peptide to the protein,
   b) ability to stimulate glucose uptake in an adipocyte after specific binding of a phosphoinositolglycan or a phosphoinositolglycan-peptide to the protein and
   c) molecular weight of protein is 115 kDa.

2. The isolated protein of claim 1 wherein the phosphoinositolglycan or phosphoinositolglycan-peptide consists of at least one compound of the following group: Tyr-Cys-Asn-NH—$(CH_2)_2$—O—PO(OH)O-6Man α1-2)-2Man α1-6Man α1-4GluN1-6Ino-1,2-(cyclic)-phosphate (YCN-PIG), peptide variant of YCN-PIG(YMIN-PIG), HO—PO(H)O-6Manα1(Manα1-2)-2-Manα1-6Manα1-4GluN1-6Ino-1,2-(cyclic)-phosphate (PIG37), Tyr-Cys-Asn-NH—$(CH_2)_2$—OH (YCN) and lipolitically cleaved glycosylphosphatidylinositol (IcGce1).

3. The isolated protein of claim 1 wherein the phosphoinositolglycan or phosphoinositolglycan-peptide binds to the protein with a binding constant of 0.001 to 10 µM.

4. The isolated protein of claim 1 wherein the phosphoinositolglycan or phosphoinositolglycan-peptide binds with a binding constant of 0.001 to 1 µM.

5. The isolated protein of claim 1 wherein the adipocyte is of rat, mouse or human origin.

* * * * *